United States Patent [19]

Yamamura et al.

[11] 4,314,998
[45] Feb. 9, 1982

[54] 6-DEOXYGLUCOSAMINE-PEPTIDE DERIVATIVES, THEIR PRODUCTION AND USE

[75] Inventors: Yuichi Yamamura, Takarazuka; Akira Hasegawa, Gifu; Ichiro Azuma, Sapporo; Shigeru Kobayashi, Osaka, all of Japan

[73] Assignee: Takeda Chemical Industries, Ltd., Osaka, Japan

[21] Appl. No.: 123,812

[22] Filed: Feb. 22, 1980

[30] Foreign Application Priority Data

Feb. 28, 1979 [JP] Japan .................................. 54-23689
Jan. 8, 1980 [JP] Japan .................................. 55-1201

[51] Int. Cl.³ .................... A61K 37/00; A61K 37/02; C07C 103/52
[52] U.S. Cl. .............................. 424/177; 260/112.5 R
[58] Field of Search .............................. 424/177, 88; 260/112.5 R

[56] References Cited

FOREIGN PATENT DOCUMENTS 6068 12/1979 European Pat. Off. .

OTHER PUBLICATIONS

Derwent Abstracts, No. 41683y/84, Belgium Patent 849214, 1975.
Derwent Abstracts, No. 65011y37, Belgium Patent 852348, 1977.

Primary Examiner—Blondel Hazel
Attorney, Agent, or Firm—Wegner & Bretschneider

[57] ABSTRACT

Novel 6-deoxyglucosamine-peptide derivatives of the formula

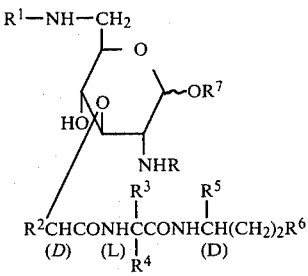

wherein
R is hydrogen or an organic acid residue or alkoxycarbonyl;
$R^1$ is hydrogen or acyl;
$R^2$ is hydrogen or lower alkyl;
$R^3$ and $R^4$ are each hydrogen or lower alkyl which may be substituted with hydroxyl;
$R^5$ and $R^6$ are each carboxyl which may be esterified or amidated;
$R^7$ is hydrogen or aralkyl; and
(D) and (L) each indicate configurations if their respective carbon atoms are asymmetric or a salt thereof having immunostimulatory activity.

13 Claims, No Drawings

6-DEOXYGLUCOSAMINE-PEPTIDE DERIVATIVES, THEIR PRODUCTION AND USE

The present invention relates to novel and useful glucosamine-peptide derivatives.

The present inventors have succeeded in producing novel 6-deoxyglucosamine-peptide derivatives of the formula

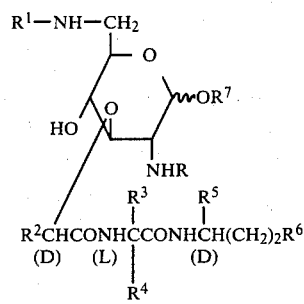

wherein
R is hydrogen, an organic acid residue or alkoxycarbonyl;
$R^1$ is hydrogen or acyl;
$R^2$ is hydrogen or lower alkyl;
$R^3$ and $R^4$ are each hydrogen or lower alkyl which may be substituted with hydroxyl;
$R^5$ and $R^6$ are each carboxyl which may be esterified or amidated;
$R^7$ is hydrogen or aralkyl; and
(D) and (L) each indicate configurations if their respective carbon atoms are asymmetric
or salts thereof.

Further studies on the compounds of the formula (I) have unexpectedly revealed that these compounds and salts thereof exhibit excellent immunostimulatory activity, especially cell-mediated immunostimulatory activity, and are of value, for example, as antiinfectious agents, antitumour agents or immunoadjuvants.

Thus, the principal object of the present invention is to provide the novel and useful compounds (I) and salts thereof which have excellent immunostimulatory activity, and another object is to provide an industrially advantageous process for producing the above compounds of the formula (I) and the salts thereof. Other objects will be made clear from the description and claims presented hereinafter.

Referring to the formula (I), the alkoxycarbonyl represented by R is preferably lower alkoxycarbonyl such as t-butyloxycarbonyl group and, the organic acid residual represented by R includes those of organic acids, for example, carboxylic acids such as acetic acid, propionic acid, glycolic acid, benzoic acid which may have substituent(s), etc., or organic sulfonic acids such as methanesulfonic acid, ethanesulfonic acid, benzenesulfonic acid which may have substituent(s).

An acyl group having an acyclic hydrocarbon group, the terminal of which may optionally be substituted with a cyclic hydrocarbon group for R or $R^1$ may be either straight-chain or a branched, and may be either saturated or unsaturated. In the case of the unsaturated hydrocarbon chain, the multiple bonds present may be isolated from each other or conjugated. Where there is a double bond, the main chain may be in either cis or trans form across the double bond. Generally, the acyclic hydrocarbon group having up to 80 carbon atoms is preferred and representative examples of the acyl group include acetyl, propionyl, butyroyl, valeroyl, nonanoyl, palmitoyl, stearoyl, oleoyl, geranylacetyl, digeranylacetyl, farnesylacetyl, geranylgeranylacetyl, di(farnesylfarnesyl)acetyl etc., as well as carboxylic acid residue of organic acids obtainable from microbacterial cells by extraction and separation, for example, mycolic acid obtained from Mycobacteria, nocardomycolic acid obtained from Nocardia, corynomycolic acid obtained from Corynebacteria.

The cyclic hydrocarbon group which may be present as the substituent at the terminal of the acyclic hydrocarbon group may preferably be an unsaturated 6-membered or fused 10-membered hydrocarbon group, such as phenyl, cyclohexenyl, cyclohexadienyl, dihydronaphthyl, etc. The cyclic hydrocarbon group can contain substituent(s) such as lower alkyl group(s) (e.g. methyl, ethyl, isopropyl, etc., preferably those having up to 3 carbon atoms), lower alkoxyl group(s) (e.g. methoxy, ethoxy, propoxy etc., preferably those having up to 3 carbon atoms) or/and oxo group(s). Among them, 2,3-dimethoxy-5-methyl-1,4-benzoquinon-6-yl is most preferred. Examples of the acyl group, the terminal of which is substituted with the above cyclic hydrocarbon group, include 3-(2,3-dimethoxy-5-methyl-1,4-benzoquinon-6-yl)propionyl, 6-(2,3-dimethoxy-5-methyl-1,4-benzoquinon-6-yl)hexanoyl, 10-(2,3-dimethoxy-5-methyl-1,4-benzoquinon-6-yl)decanoyl, retinoyl, 6-(2,3,5-trimethyl-1,4-benzoquinon-6-yl)-4-methyl-4-hexenoyl, 6-(2,3-dimethoxy-5-methyl-1,4-benzoquinon-6-yl)-4-methyl-4-hexenoyl, 6-(2-methyl-1,4-naphthoquinon-3-yl)-4-methyl-4-hexenoyl, 4-(2,3,5-trimethyl-1,4-benzoquinon-6-yl)-2-methylbutyroyl, 4-(2,3-dimethoxy-5-methyl-1,4-benzoquinon-6-yl)-2-methylbutyroyl, 10-(2,3,5-trimethyl-1,4-benzoquinon-6-yl)decanoyl, 4-(2-methyl-1,4-naphthoquinon-3-yl)-2-methylbutyroyl, 9-(2-methyl-1,4-naphthoquinon-3-yl)nonanoyl, 6-(2,3,5-trimethyl-1,4-benzoquinon-6-yl)hexanoyl, 5-(2-methyl-1,4-naphthoquinon-3-yl) pentanoyl, 3-[{3,4-dihydro-2,5,7,8-tetramethyl-2-(4,8,12-trimethyltridecyl)-2H-1-benzopyran-6-yl}oxycarbonyl]propanoyl, 3,7-dimethyl-9-(2,6,6-trimethyl-1-cyclohexen-1-yl)-2,4,6,8-nonatetraenoyl and the like.

Among the acyl groups described above, the acyl group having a hydrocarbon chain of 11–80 carbon atoms, the terminal of which is not substituted with any cyclic hydrocarbon group, and the acyl group having a hydrocarbon chain of 2–10 carbon atoms, the terminal of which is substituted with the above-mentioned cyclic hydrocarbon group, etc. are preferred.

The lower alkyl group for $R^2$, $R^3$ and $R^4$ can be a straight-chain or a branched, preferably having up to 6 carbon atoms. Examples of lower alkyl groups are methyl, ethyl, n-propyl, isopropyl, or butyl or pentyl which can be of straight-chain or of a chain branched at any position of the chain, with the alkyl group having up to 3 carbon atoms being preferred.

$R^5$ and $R^6$ each is preferably a carboxyl group which may be esterified with a lower alkyl group such as methyl, ethyl, propyl and the like or amidated (optionally alkylamidated with a lower alkyl group), and $R^5$ is most preferably a carbamoyl group or a carboxyl group esterified with a lower alkyl group and $R^6$ is most preferably a carboxyl group or a carboxyl group esterified with a lower alkyl group.

$R^7$ is preferably a hydrogen atom or an aralkyl group such as benzyl, phenethyl and the like, and the benzene moiety contained in the aralkyl group may be substituted with halogen atom(s), lower alkyl group(s), nitro group(s), etc. When $R^7$ represents a hydrogen atom, the sugar moiety can be both the pyranose structure such as the formula (I) and the open-ring aldose structure, in the same manner as usual hexose.

Of these compounds of the formula (I) above, a compound wherein R is an acetyl group and $R^2$ is a methyl group is particularly preferred. Further, when $R^3$ is a hydrogen atom, $R^4$ is preferably a lower alkyl group, a hydroxymethyl group or a 1-hydroxyethyl group and, when $R^3$ is a lower alkyl group, $R^4$ is preferably a lower alkyl group.

In the compounds (I) above, the glucosamine residue is preferably of the D-configuration, and the $R^2$-substituted acetic acid residue attached to the oxygen atom at the 3-position thereof is preferably of the D-configuration. Also, $R^3$- and $R^4$-substituted aminoacyl residue is preferably of the L-configuration when both $R^3$ and $R^4$ are not hydrogen atoms or the same lower alkyl groups, and $R^5$-substituted amino acid is preferably of the D-configuration.

The compounds (I) are acidic, basic or neutral, depending upon the type of substituents, and when the compounds are acidic, they can form salts with bases. Examples of salts with bases are ammonium salts, alkali metal or alkaline earth metal salts such as sodium, potassium, calcium or magnesium salt. When the compounds are basic, they can form salts with acids, for example, inorganic acids, e.g. hydrochloric acid, hydrobromic acid, phosphoric acid, nitric acid, sulfuric acid, etc., an organic carboxylic acid, e.g. acetic acid, propionic acid, maleic acid, succinic acid, malic acid, citric acid, tartaric acid, salicyclic acid, nicotinic acid etc., or an organic sulfonic acid, e.g. methanesulfonic acid, p-toluenesulfonic acid etc. The compounds (I) may be used as the physiologically acceptable salts with these bases or acids.

The compounds (I) of the present invention have low toxicity and a potent stimulating activity on the immunological functions. Particularly, the compounds (I) significantly enhance the cell-mediated immunity, which play a major role for the anti-infection and suppressive effect on cancer. This fact can be established by the following experiments.

The ability of the compound (I) to stimulate the cell-mediated immunity of recipient hosts can be established by their immunoenhancing effect on the induction of delayed type hypersensitivity to azobenzenearsonate N-acetyl-L-tyrosine (ABA-N-Ac-Tyr) in guinea pigs. Thus, a mixed solution of ABA-N-Ac-Tyr (50 µg per animal) and the compound (I) of this invention (10–200 µg per animal) in phosphate-buffered saline was admixed with Freund's incomplete adjuvant to prepare a water-in-oil emulsion and guinea pigs (Hartley strain) were immunized by injecting the emulsion into the footpad (sole) of each animal in a dose of 0.05 ml. After 2 weeks the back of each animal was shaved and ABA-bacterial α-amylase [ABA-BαA] (100 µg) was intrperitoneally administered. After 24 and 48 hours, the diameters of skin reactions (erythema and induration) were measured. These diameters serve as a measure of cell-mediated immunity.

As a control, when a solution of ABA-N-Ac-Tyr, which is the antigen, alone in phosphate-buffered saline was admixed with Freund's incomplete adjuvant to prepare a water-in-oil emulsion and this emulsion was similarly administered, there was induced to delayed type hypersensitivity to ABA-N-Ac-Tyr. This experiment indicates that the compounds in accordance with the present invention possess strong activity to reinforce immunity against cellular immune reactions (delayed hypersensitivity).

The cell-mediated immunostimulatory activity of the compounds (I) is also evident from the fact that they are able to markedly amplify the onset of cytotoxicity [The induction of lymphocytes specifically toxic to target cells (cancer cells)]. Thus, C57BL/6J mice (H-$a^b$) are intraperitoneally injected with Mastocytoma P815-X2(H-$2^d$) are intraperitoneally injected with Mastocytoma P815-X2(H-$2^d$) cells, with or without one of the compounds according to this invention as dissolved in phosphate-buffered saline. On the 11th day after this immunization, the spleen of each mouse is enucleated and the T-cell (killer-T cell cytotoxic to the target cells) population in the spleen is determined by the method of Brunner (Immunology 18, 501–515). The concurrent administration of compounds (I) and said Mastocytoma cells resulted in a marked increase in the killer-T cell population in the spleen. Immunotherapy of cancer designed to reject nonautologous cancer cells by increasing the immunological responsiveness of the patient has been widely practiced in recent years and the killer-T cell is thought to play a major role in this therapy. Therefore, the killer-T cell population as stimulated by the administration of the compounds (I) may be regarded as a measure of antitumour activity.

For example, 100 µg of the compounds obtained in accordance with the present invention suspended in a phosphate-buffered saline and mixed with $5 \times 10^4$ Meth-A fibrosarcoma cells, followed by intracutaneous administration to female Balb/C mice. The effects to inhibit the growth of Meth-A were examined at 1 week intervals until the 4th week after the administration. As a result, strong inhibiting effects were observed and the results obtained are shown in Table below.

| Test sample | Dosage (µg) | The number of tumor-free mice/ the number of mice tested | | | |
|---|---|---|---|---|---|
| | | 1 | 2 | 3 | 4(week) |
| 2-(2-Acetamido-2,6-dideoxy-6-mycoloyl-amino-D-gluco-pyranos-3-0-yl)-D-propionyl-L-alanyl-D-isoglutamine (Example 7) | 100 | 10/10 | 10/10 | 10/10 | 10/10 |
| 2-(2-Acetamido-2,6-dideoxy-6-mycoloyl-amino-D-gluco-pyranos-3-0-yl)-D-propionyl-L-valyl-l-isoglutamine (Example 9) | 100 | 10/10 | 10/10 | 10/10 | 10/10 |
| Control | — | 1/10 | 0/10 | 0/10 | 0/10 |

By virtue of the aforementioned properties, the compounds (I) according to this invention can be employed for the treatment of many diseases attributable to cell-mediated immunity depressions, for example, as antiinfectious agents (e.g., for suppressing enteritis and pneumonia) and as antiumor agent (e.g., for inhibiting in warm-blooded animals tumors such as lung cancer and malignant melanoma).

On the one hand, because the compound (I) are capable of stimulating the immunogenicity of an antigen when used in combination therewith, they are suitable for use as an admixture with various antigens for the production of diagnostic and therapeutic antisera. Moreover, the compounds (I) can be employed for the purpose of potentiating the immunity already latent in the body without concomitant addition of antigens.

Therefore, the compounds (I) are particularly effective in the treatment of hosts with chronic and acute infectious disease, hosts with congenital immunodeficiency, hosts who acquired impaired immunity, for example, in the course of a serious primary disease at an advanced age, and cancer-bearing hosts subjected to chemotherapy, radiation therapy, or other therapy which is immunosuppressive. The compounds (I) are also useful as prophylactic agents for recipients with increased susceptibility to cancer because of decreased immunological functions caused by, for example, aging, and for recipients who are in an environment which leads to increased incidence of cancer.

The compounds (I) can thus be administered to warm-blooded animals (e.g. man; laboratory animals such as mouse, guinea pig, rat, etc.; pet animals such as dog, cat, etc.) either enterally, e.g. orally or rectally, or parenterally. The dosage depends on the individual conditions of the animal, its species and age and the dosage form used. When, for example, the compound is used as an injectable isotonic solution, e.g. an isotonic aqueous solution such as a salt-containing solution or a glucose solution, for subcutaneous, intracutaneous or intramuscular administration, the preferred dosage as infectious agents, or to inhibit the tumor growth of lung cancer or malignant melanoma may range from 1 to 500 μg/kg/day (as the anhydrate of the compound) and, particularly, from about 5 to 30 μg/kg/day (on the same basis).

For such parenteral administration, the compound may also be administered in the form of a stabilized water-in-oil emulsion, the oil being preferably of the vegetable or animal origin. Such a vegetable or animal oil emulsion may comprise about 5 to 100 volume parts of the isotonic aqueous solution and one volume part of a metabolizable vegetable or animal oil, supplemented with an emulsion stabilizer, for instance.

For administration by the oral route, the compound may be formulated with a pharmaceutically acceptable excipient and used as sugar-coated tablets, capsules, etc., the dosage in such forms being between about 40 and 4000 μg/kg/day.

The compounds of the formula (I) of the present invention can be obtained, for example by reducing the compound represented by the formula

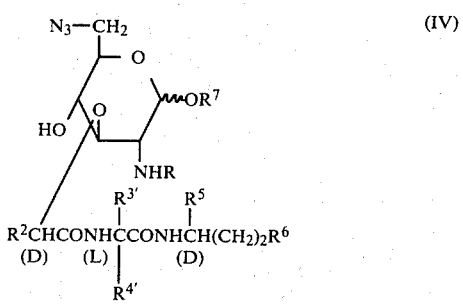

(IV)

wherein R, $R^2$, $R^5$, $R^6$, $R^7$, (D) and (L) are as defined above, and $R^{3'}$ and $R^{4'}$ each represents the group defined by $R^3$ and $R^4$, respectively, or the group defined by $R^3$ and $R^4$ where the hydroxyl group thereof is protected, and optionally removing the protective group; or further condensing the compound obtained by removing a part of the protective groups, represented by the formula:

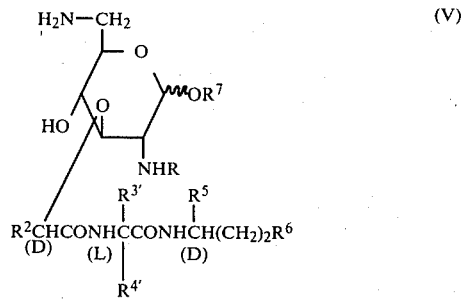

(V)

wherein R, $R^2$, $R^{3'}$, $R^{4'}$, $R^5$, $R^6$, $R^7$, (D) and (L) are as defined above, with a compound represented by the formula

$R^{1'}$—OH (III)

wherein $R^1$ is an acyl group, and then optionally removing the protective group and, provide that R in the formula (V) is hydrogen atom, compound (I) wherein $R = R^1 = R^{1'}$ can be obtained at one stroke or by condensing a compound represented by the formula

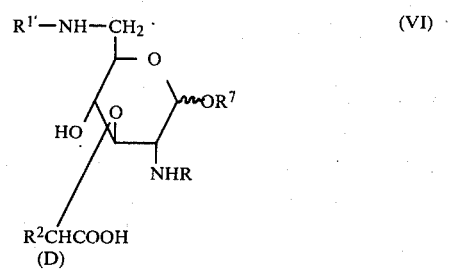

(VI)

wherein R, $R^{1'}$, $R^2$, $R^7$ and (D) are as defined above, with a compound of the formula:

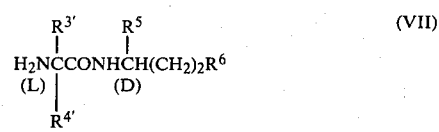

(VII)

wherein $R^{3'}$, $R^{4'}$, $R^5$, $R^6$, (D) and (L) are as defined above, and optionally removing the protective group.

The protective group for the hydroxyl group contained in the groups represented by $R^{3'}$ and $R^{4'}$ with respect to the compounds of the formulae (IV), (V) and (VII) can each be any known protective group which can be easily removed, for example, an alkyl group such as a tertiary butyl group, a tetrahydropyranyl group, a benzoylcarbonyl group or a lower alkanoylcarbonyl group, and, in particular, a benzyl group which may be substituted with halogen atom(s) or nitro, lower alkyl or lower alkoxyl group(s) can be used conveniently.

The reduction of the compound (IV) can be achieved by a conventional procedure. For example, the most general procedure which can be used is a catalytic reduction comprising reacting the compound (IV) with hydrogen in the presence of a catalyst. The catalyst used for the catalytic reduction is preferably a metal catalyst, for example, platinum, palladium, rhodium, lutenium, Raney nickel and the like. These metal catalysts can be used as free, finely divided metal powder or can be deposited on carbon, alumina, barium sulfate, calcium carbonate, strontium carbonate and the like. Further, copper chromite produced from copper and chromium oxide can also be used. The solvent, hydrogen pressure and reaction temperature used for the catalytic reduction should be suitably selected depending upon the type of a catalyst used, but generally, ethyl acetate, methanol, ethanol, dioxane, tetrahydrofuran, water, N,N-dimethylformamide, acetic acid, acetic acid containing perchloric acid, etc. can be used as a solvent.

The hydrogen pressure used for the reaction can be suitably selected between atmospheric pressure to about 300 atms., but when the catalyst containing platinum, palladium or rhodium, or Raney nickel having a high catalytic activity is used, a hydrogen pressure from atmospheric pressure to about 4 atms. is generally sufficient. Further, instead of using hydrogen gas, an acid and an excess of sodium borohydride can be used in the reaction system to generate hydrogen required for the catalytic reduction.

The reaction temperature can be relatively low (0° C. to 100° C.) and, in most instances, the reaction is effected at a temperature from room temperature to about 50° C. The protective group may also be removed simultaneously by the hydrogenation, but, if desired, other protective groups can be removed hydrolytically by treatment with an acid.

The compound (V) thus obtained can be optionally condensed with the compound represented by the formula (III). The condensation reaction per se used above can be effected by a known procedure, for example, by reacting the compound (III) having an activated carboxyl group with the compound (V).

Examples of activated carboxyl groups are active esters, acid anhydrides, acid halides and the like.

Examples of active esters are a cyanomethyl ester, a thioglycolic acid ester, a p-nitrophenyl ester, a 2,4,5-trichlorophenyl ester, a pentachlorophenyl ester, a pentafluorophenyl ester, a pivarohydroxanthic acid ester, an N-hydroxyphthalimide ester, an N-hydroxysuccinimide ester, an N-hydroxy-5-norbornene-2,3-dicarboximide ester, an 8-hydroxyquinolyl ester, a 2-hydroxy-1,2-dihydro-1-carboethoxyquinolyl ester, a 2-hydroxyphenyl ester, a 2-hydroxy-4,5-dichlorophenyl ester, a 2-hydroxypyridyl ester, a 2-pyridylthiol ester, a 1-hydroxybenzotriazol ester, which can be unsubstituted or substituted with a halomethyl or methoxy group, or an enol ester obtained by using an N-ethyl-5-phenylisoxazolium-3-sulfonate, and the like.

Examples of acid anhydrides are preferably a mixed acid anhydride, an acid amide, e.g., imidazolide, isoxazolide and the like.

Examples of acid halides are preferably an acid chloride and an acid bromide.

The activation of the carboxyl group can also be achieved by directly reacting the compound (III) with N,N'-dicyclohexylcarbodiimide.

The reaction of the activated ester can be conducted, if necessary, in the presence of an organic base, for example, triethylamine, N-methylmorpholine, N-ethylmorpholine or 1-hydroxybenzotriazole.

The reaction temperature is generally from about 0° C. to about 80° C., preferably about 5° to about 50° C. The reaction can be conducted at a temperature outside the above range, if desired.

The reaction generally proceeds in a solvent, and various solvents, for example, ethers such as tetrahydrofuran, dioxane, etc., esters such as ethyl acetate, isoamyl acetate, etc., N-alkylamides such as N,N-dimethylformamide, N-methyl-2-pyrrolidone, N,N-dimethylacetamide, etc., as well as other solvents such as dimethylsulfoxide, hexamethylphosphoramide and the like can be suitably used.

The above compound (III) reacts with the compound (V) stoichiometrically, but these two reactants need not necessarily be present in the reaction system in equimolar proportions and generally the compound (III) or an active derivative thereof is used in an amount of about 1 to 5 moles, preferably 1 to 2 moles, per 1 mole of the compound (V). The proportions of these two reactants can be suitably selected depending upon the specific combination of the reactants and other conditions so as to attain an optimum result. Further, unreacted starting materials can be recovered and re-used as starting materials.

After completion of the above reaction, the protective group can be removed, if necessary, by a procedure which is known per se. For example, the protective group can be preferably removed by catalytic hydrogenolysis in the presence of a metal catalyst or by hydrolysis with an acid.

Further, the compound represented by the formula (I) can be prepared by condensing the compound (VI) and the compound (VII) and, optionally, removing the protective group. The condensation reaction between the compound (VI) and the compound (VII) can be achieved in the same manner as described previously for the condensation of the compound (III) and compound (V). The optional removal of the protective group can also be effected in the same manner as described previously.

Similarly, the compound represented by the formula (I) can be produced by any method which is different from known methods, in respect of the reaction order. For example, compound (I) can also be obtained by the reaction of the formula

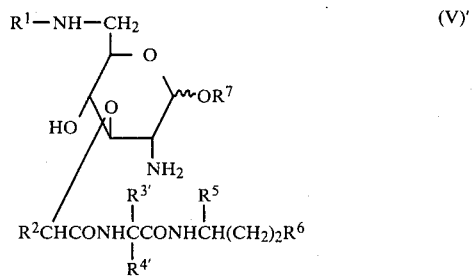

(V)' wherein all the designations are of the same meanings as respectively defined hereinbefore, and the formula

wherein R' is the same as R excluding hydrogen atom.

The compound (I) thus produced can be isolated as a free form or as the salt form as described above by utilizing conventional work-up, for example, extraction, trans-dissolution, chromatography, crystallization, recrystallization, reprecipitation and the like.

The starting compound (IV) can be prepared by converting the hydroxyl group of the sugar moiety of the compound represented by the formula

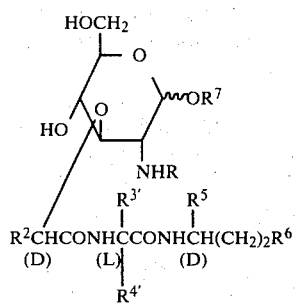

(VIII)

wherein R, $R^2$, $R^{3'}$, $R^{4'}$, $R^5$, $R^6$, $R^7$, (D) (L) are as defined above, into an azide group by the procedure which is per se known in the art. In this conversion, a procedure comprising, for example, converting the hydroxyl group at the 6-position of the sugar moiety into a sulfonic acid ester and the resulting ester into an azido group is preferably used.

Examples of sulfonating agents used above are lower alkyl sulfonyl chlorides, e.g., methanesulfonyl chloride and the like, or benzenesulfonyl chlorides which may be substituted with a lower alkyl group, e.g., p-toluenesulfonyl chloride and the like. The reaction can be conducted in the presence of an organic base, e.g., pyridine, triethylamine, N-ethylmorpholine, etc. and solvents such as those described above can be suitably used. The reaction temperature is generally from about 0°0 C. to about 50° C., preferably 0° C. to room temperature, but the reaction can be conducted, if desired, at a temperature outside the above range.

The 6-O-sulfonyl compound of the formula (VIII) thus obtained can then be reacted with, for example, sodium azide to obtain the desired 6-azide compound (IV). The reaction temperature employed for the azide formation reaction can be from room temperature to about 200° C., preferably from room temperature to about 80° C. If desired, the reaction can be effected at a temperature outside the above range. The reaction generally proceeds in a solvent and solvents suitably selected from, for example, those described above, can be suitably used.

In the above two-step reactions, a sulfonyl chloride, sodium azide, etc. reacts stoichiometrically with a sugar peptide moiety, but in each of these reactions the two reactants are, of course, not necessarily required to be present in an equimolar ratio in the reaction system and, generally, sulfonyl chloride or sodium azide is used in an amount of about 1 to about 20 moles, preferably 1 to 10 moles, per 1 mole of the sugar peptide compound. The proportion of these two reactants can be suitably selected depending upon the specific combination of the reactants and other conditions so as to attain an optimum result. Further, unreacted starting materials can be recovered and can be re-used as starting materials.

The compound (IV) thus produced can be isolated by the procedure which is per se known as described above.

The starting compound (V') can be produced from compound (IV), R means an alkoxycarbonyl group in this case, by the method known per se.

Further, starting compound (VI) can be easily prepared by converting a hydroxyl group at the 6-position of the compound represented by the formula

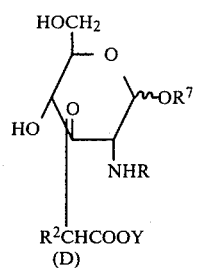

(IX)

wherein R, $R^2$, $R^7$ and (D) are as defined above, and Y represents a protective group for the carboxyl group, to an amino group, condensing the resulting compound with the compound (III) and removing the protective group Y prior to or after the above condensation reaction.

The protective group represented by Y for the carboxyl group in the above formula (IX) can be any protective group which is well known in the art of peptide chemistry and which can easily be removed, for example, a methyl group, an ethyl group, a t-butyl group, a benzyl group, a p-methoxybenzyl group, a benzhydryl group, etc.

The conversion of the 6-hydroxyl group of the compound (IX) to the amino group can be achieved in the same manner as described above for the production of the compound (V) from the compound (VIII), and the condensation reaction of the resulting amino compound with the compound (III) can also be achieved in the same manner as described above for the condensation reaction between the compound (III) and compound (V). Further, the removal of the protective group Y for the carboxyl group can be effected by, for example, an acid or alkali hydrolysis or a catalytic reduction in the presence of a metal catalyst.

The present invention is further illustrated in greater detail by the following Examples, but they are not to be construed as limiting the present invention. In order to simplify the description of Example 1-17, N,N-dimethylformamide is abbreviated as DMF, N,N'-dicyclohexylcarbodiimide is as DCC and N-hydroxysuccinimide ester is as HOSuc ester. Further, thin-layer chromatography is used as a means for identification of the compound produced and the developing solvent systems used in the chromatography are indicated by the following symbols:

$R_f^1$: chloroform-acetone-methanol=10:3:2, v/v;
$R_f^2$: chloroform-methanol=95:5, v/v;
$R_f^3$: chloroform-methanol-acetic acid=18:2:1, v/v: $R_f^4$: ethyl acetate-pyridine-acetic acid-water=30:10:3:5, v/v; $R_f^5$: ethyl acetate-n-butanol-acetic acid-water=1:1:1:1, v/v.

The term "$R_f^3$=0.76", for instance, used in Examples, means that the compound has a $R_f$ value of 0.76 on a silica gel plate developed with the above $R_f^3$ solvent system.

EXAMPLE 1

(I) Benzyl 2-acetamido-3-O-(D-1-carboxyethyl)-2-deoxy-4,6-O-isopropylidene-α-D-glucopyranoside (4.60 g, 10.9 mmol) was dissolved in methanol (40 ml) and refluxed for 24 hours with stirring in the presence of an ion-exchange resin, Amberlite IR-120 (H+, 30 g). The resin was filtered off and washed with methanol, and the combined filtrate and washings was concentrated under reduced pressure. The residue was purified by column chromatography (Wakogel C-300, 90 g; chloroform-methanol=50:1, v/v) to obtain 2.85 g of benzyl 2-acetamido-2-deoxy-3-O-[D-1-(methoxycarbonyl)ethyl]-α-D-glucopyranoside as crystals. Melting point, 120° C. $[\alpha]_D^{25} + 148.5°$ (c 1.0, chloroform).

Elemental analysis for $C_{19}H_{27}NO_8$: Calcd.: C, 57.42; H, 6.85; N, 3.52. Found: C, 57.53; H, 6.73; N, 3.49.

(II) Benzyl 2-acetamido-2-deoxy-3-O-[D-1-(methoxycarbonyl)ethyl]-α-D-glucopyranoside (1.78 g, 4.48 mmol) was dissolved in anhydrous pyridine (15 ml). The solution was cooled to −20° C. and methanesulfonyl chloride (670 mg, 5.83 mmol) was added to the solution, followed by stirring for 5 hours at −20° C. After completion of the reaction, water was added to the reaction mixture to decompose any excess of the reagent, and the mixture was concentrated under reduced pressure. The residue was extracted with chloroform, and the chloroform layer was washed successively with 2 N hydrochloric acid, 2 N sodium carbonate and water, dried over anhydrous sodium sulfate, and evaporated. The residue was purified by column chromatography (Wakogel C-300, 40 g; chloroform-methanol=50:1, v/v) to obtain 1.80 g of benzyl 2-acetamido-2-deoxy-6-O-mesyl-3-O-[D-1-(methoxycarbonyl)ethyl]-α-D-glucopyranoside as a syrup. $[\alpha]_D^{26} + 87°$ (c 0.6, chloroform).

Elemental analysis for $C_{20}H_{29}NO_{10}S$: Calcd.: C, 50.51; H, 6.15; N, 2.95. Found: C, 50.50; H, 6.10; N, 2.86.

(III) Benzyl 2-acetamido-2-deoxy-6-O-mesyl-3-O-[D-1-(methoxycarbonyl)ethyl]-α-D-glucopyanoside (1.84 g, 3.87 mmol) was dissolved in anhydrous DMF (15 ml) and sodium azide (1.8 g) was good to the solution, followed by heating at 80° C. for 5 hours while stirring. After completion of the reaction, inorganic substances were filtered using Celite and washed with methanol. The combined filtrate and washing was concentrated under reduced pressure and the residue was extracted with chloroform. The chloroform layer was washed successively with 2 N hydrochloric acid, 2 N sodium carbonate and water, dryed over anhydrous sodium sulfate, and evaporated. The residue was purified by column chromatography (Wakagel C-300, 50 g chloroform-methanol=100:1, v/v) to obtain 1.19 g of benzyl 2-acetamido-6-azido-2,6-dideoxy-3-O-[D-1-(methoxycarbonyl)ethyl]-α-D-glucopyranoside as crystals. Melting point, 120° C. $[\alpha]_D^{27} + 118°$ (c 0.6, chloroform).

Elemental analysis for $C_{19}H_{26}N_4O_7$: Calcd: C, 54.02; H, 6.20; N, 13.26. Found: C, 53.86; H, 6.33; N, 13.51.

(IV) Benzyl 2-acetamido-6-azido-2,6-dideoxy-3-O-[D-1-(methoxycarbonyl)ethyl]-α-D-glucopyranoside (1.00 g, 2.4 mmol) was dissolved in dioxane (15 ml), and a 0.1 N potassium hydroxide solution (30 ml) was added to the solution, followed by stirring for 5 minutes at 15° C. After completion of the reaction, an ion-exchange resin, Amberlite IR-120 (H+), was added to the reaction mixture to remove potassium. The resin was filtered, and washed with methanol. The combined filtrate and washing was concentrated under reduced pressure at a temperature below 45° C. and the residue was recrystallized from ethanol-diethyl ether to obtain 0.95 g of benzyl 2-acetamido-6-azido-3-O-(D-1-carboxyethyl)-2,6-dideoxy-α-D-glucopyranoside as crystals. Melting point, 182° C. $[\alpha]_D^{22} + 137.9°$ (c 0.7, methanol).

Elemental analysis for $C_{18}H_{24}N_4O_7$: Calcd.: C, 52.93; H, 5.92, N, 13.72. Found: C, 52.86; H, 5.92; N, 13.88.

(V) Benzyl 2-acetamido-6-azido-3-O-(D-1-carboxyethyl)-2,6-dideoxy-α-D-glucopyranoside (140 mg, 0.34 mmol) was dissolved in dioxane (3 ml) and N-hydroxysuccinimide (48 mg, 0.42 mmol) and DCC (85 mg, 0.41 mmol) were added to the solution at room temperature. After stirring the mixture at room temperature for one hour, the precipitate was filtered and washed with dioxane (4 ml). To the combined filtrate and washing were added L-alanyl-D-isoglutamine benzyl ester trifluoroacetate (205 mg, 0.41 mmol) and triethylamine (0.06 ml, 0.43 mmol), and, after stirring for 4 hours at room temperature, the precipitate was filtered. The filtered precipitate was recrystallized from methanol-chloroform to obtain 160 mg of benzyl 2-(benzyl 2-acetamido-6-azido-2,6-dideoxy-α-D-glucopyranosid-3-O-yl)-D-propionyl-L-alanyl-D-isoglutaminate as crystals. Melting point 210°–212° C. (decomposition). $[\alpha]_D^{25} + 61.5°$ (c 1.5, acetic acid).

Elemental analysis for $C_{33}H_{43}N_7O_{10}$: Calcd.: C, 56.81; H, 6.21; N, 14.05. Found: C, 56.77; H, 6.15; N, 14.11.

(VI) Benzyl 2-(benzyl 2-acetamido-6-azido-2,6-didoexy-α-D-glucopyranosid-3-O-yl)-D-propionyl-L-alanyl-D-isoglutaminate (100 mg, 0.14 mmol) was dissolved in a mixture of acetic acid (10 ml), methanol (5 ml) and water (10 ml) and the mixture was hydrogenated at 40° C. for 2.5 hours in the presence of palladium black. After removal of the catalyst, the solvent was evaporated and the residue was purified by column chromatography (Wakogel C-200, 15 g; chloroform-methanol=1:1, v/v), to obtain 22 mg of 2-(2-acetamido-6-amino-2,6-dideoxy-D-glucopyranos-3-O-yl)-D-propionyl-L-alanyl-D-isoglutamine as crystals. Melting point, 133°–134° C. (decomposition).

Elemental analysis for $C_{19}H_{33}N_5O_{10}$: Calcd.: C, 46.43; H, 6.77; N, 14.25. Found: C, 46.12; H, 6.99; N, 13.98.

EXAMPLE 2

(I) Benzyl 2-acetamido-6-azido-3-O-(D-1-carboxyethyl)-2,6-dideoxy-α-D-glucopyranoside (140 mg, 0.34 mmol) was reacted with N-hydroxysuccinimide (48 mg, 0.42 mmol) in the presence of DCC (85 mg, 0.41 mmol) in dioxane (3 ml) at room temperature in the same manner as described in Example 1-(V) and thereafter further reacted with L-valyl-D-isoglutamine benzyl ester (138 mg, 0.41 mmol) to obtain 175 mg of benzyl 2-(benzyl 2-acetamido-6-azido-2,6-dideoxy-α-D-glucopyranosid-3-O-yl)-D-propionyl-L-valyl-D-isoglutaminate as crystals. Melting point, 223°–224° C. (decomposition). $[\alpha]_D^{20} + 75.2°$ (c 0.6, acetic acid).

Elemental analysis for $C_{35}H_{47}N_7O_{10}$: Calcd.: C, 57.92; H, 6.53; N, 13.51. Found: C, 57.56; H, 6.50; N, 13.38.

(II) Benzyl 2-(benzyl 12-acetamido-6-azido-2,6-dideoxy-α-D-glucopyranosid-3-O-yl)-D-propionyl-L-valyl-D-isoglutaminate (100 mg, 0.14 mmol) was hydrogenated in a mixture of acetic acid (10 ml), methanol (5 ml) and water (10 ml) in the presence of palladium black (200 mg), and then worked up and purified in the same manner as described in Example 1-(VI) to obtain 22 mg of 2-(2-acetamido-6-amino-2,6-dideoxy-D-glucopyranos-3-O-yl)-D-propionyl-L-valyl-D-isoglutamine as crystals. Melting point, 144°–145° C. (decomposition).

Elemental analysis for $C_{21}H_{37}N_5O_{10}$: Calcd.: C, 48.54; H, 7.18; N, 13.48. Found: C, 48.23; H, 7.50; N, 13.25.

EXAMPLE 3

(I) Benzyl 2-acetamido-6-azido-3-O-(D-1-carboxyethyl)-2,6-dideoxy-α-D-glucopyranoside (500 mg, 1.23 mmol) was reacted with N-hydroxysuccinimide (173 mg, 1.47 mmol) in the presence of DCC (303 mg, 1.47 mmol) in dioxane (7 ml) in the same manner as described in Example 1-(V) and thereafter further reacted with O-benzyl-L-seryl-D-isoglutamine benzyl ester (504 mg. 1.22 mmol) at room temperature for 24 hours. The reaction solvent was then evaporated under reduced pressure and the residue was purified by column chromatography (Wakogel C-300, 40 g; chloroform-methanol=20:1, v/v) to obtain 240 mg of benzyl 2-(benzyl 2-acetamido-6-azido-2,6-dideoxy-α-D-glucopyranosid-3-O-yl)-D-propionyl-O-benzyl-L-seryl-D-isoglutaminate as crystals. Melting point, 200°–202° C. (decomposition). $[\alpha]_D^{20}+62.5°$ (c 0.4, acetic acid).

Elemental analysis for $C_{40}H_{49}N_7O_{11}$: Calcd.: C, 59.76; H, 6.14; N, 12.20. Found: C, 59.58; H, 6.06; N, 12.35.

(II) Benzyl 2-(benzyl 2-acetamido-6-azido-2,6-dideoxy-α-D-glucopyranosid-3-O-yl)-D-propionyl-O-benzyl-L-seryl-D-isoglutaminate (50 mg, 0.06 mmol) was hydrogenated in a mixture of acetic acid (10 ml), methanol (5 ml) and water (10 ml) in the presence of palladium black (100 mg) as a catalyst, and then worked up and purified in the same manner as described in Example 1-(VI) to obtain 10 mg of 2-(2-acetamido-6-amino-2,6-dideoxy-D-glucopyranos-3-O-yl)-D-propionyl-L-seryl-D-isoglutamine as crystals. Melting point 135°–136° C. (decomposition).

Elemental analysis for $C_{19}H_{33}N_5O_{11}$: Calcd.: C, 44.96; H, 6.55; N, 13.80. Found: C, 44.75; H, 6.83; N, 13.62.

EXAMPLE 4

Benzyl 2-(benzyl 2-acetamido-6-azido-2,6-dideoxy-α-D-glucopyranosid-3-O-yl)-D-propionyl-L-alanyl-D-isoglutaminate (100 mg, 0.14 mmol) was dissolved in a mixture of acetic acid (10 ml), methanol (5 ml) and water (10 ml) and hydrogenated in the presence of palladium black (200 mg) as a catalyst at 40° C. for 2.5 hours. After filtration and evaporation, the residue was dissolved in a mixture of DMF (2 ml) and dioxane (3 ml), and caprylic acid HOSuc ester (60 mg, 0.25 mmol) and triethylamine (0.01 ml) were added to the solution, followed by stirring at room temperature for 24 hours. The reaction solvent was evaporated under reduced pressure, and the residue was purified by column chromatography (Wakogel C-300, 13 g; chloroform-methanol=5:1 v/v) to obtain 28 mg of 2-(2-acetamido-2,6-dideoxy-6-octanoylamino-D-glucopyranos-3-O-yl)-D-propionyl-L-alanyl-D-isoglutamine as crystals. Melting point, 118°–119° C. (decomposition).

Elemental analysis for $C_{27}H_{47}N_5O_{11}$: Calcd.: C, 52.50; H, 7.67; N, 11.34. Found: C, 52.55; H, 7.73; N, 11.58.

EXAMPLE 5

Benzyl 2-(benzyl 2-acetamido-6-azido-2,6-dideoxy-α-D-glucopyranosid-3-O-yl)-D-propionyl-L-alanyl-D-isoglutaminate (230 mg, 0.33 mmol) was hydrogenated in the same manner as described in Example 4 and thereafter the solvent was evaporated. The resulting residue was dissolved in DMF (5 ml), and stearic acid HOSuc ester (250 mg, 0.66 mmol) and triethylamine (0.05 ml) were added to the solution, followed by stirring at room temperature for 15 hours. The reaction solvent was evaporated and the residue was purified by column chromatography (Wakogel C-300, 20 g; chloroform-methanol=10:1 v/v) to obtain 120 mg of 2-(2-acetamido-2,6-dideoxy-6-stearoylamino-D-glucopyranos-3-O-yl)-D-propionyl-L-alanyl-D-isoglutamine as crystals. Melting point, 162°–164° C. (decomposition). $[\alpha]_D^{19}+15.4°$ (after 24 hours) (c 0.28, chloroform-methanol=1:1).

Elemental analysis for $C_{37}H_{67}N_5O_{11}$: Calcd.: C, 58.63; H, 8.91; N, 9.24. Found: C, 58.58; H, 8.93; N, 9.31.

EXAMPLE 6

Benzyl 2-(benzyl 2-acetamido-6-azido-2,6-dideoxy-α-D-glucopyranosid-3-O-yl)-D-propionyl-L-alanyl-D-isoglutaminate (100 mg, 0.14 mmol) was hydrogenated in the same manner as described in Example 4 and thereafter the solvent was evaporated. The resulting residue was dissolved in a mixture of DMF (2 ml) and dioxane (3 ml), and nocardomycolic acid HOSus ester (150 mg, 0.17 mmol) and triethylamine (0.01 ml) were added to the solution, followed by stirring at room temperature for 24 hours. The reaction solvent was evaporated under reduced pressure and the residue was purified by column chromatography (Wakogel C-300, 20 g; chloroform-methanol=15:1 v/v) to obtain 90 mg of 2-(2-acetamido-2,6-dideoxy-6-nocardomycoloylamino-D-glucopyranos-3-O-yl)-D-propionyl-L-alanyl-D-isoglutamine as a waxy substance. $[\alpha]_D^{24}+7.9°$ (after 24 hours) (c 0.38, chloroform-methanol=1:1).

Elemental analysis for $C_{70}H_{128}N_5O_{12.6}$: Calcd.: C, 67.72; H, 10.39; H, 5.64. Found: C, 67.50; H, 10.53; N, 5.38.

EXAMPLE 7

Benzyl 2-(benzyl 2-acetamido-6-azido-2,6-dideoxy-α-D-glucopyranosid-3-O-yl)-D-propionyl-L-alanyl-D-isoglutaminate (150 mg, 0.22 mmol) was hydrogenated in the same manner as described in Example 4 and thereafter the solvent was evaporated. The resulting residue was dissolved in DMF (1.5 ml), and mycolic acid HOSuc ester (340 mg, 0.27 mmol) dissolved in benzene (3 ml) and then triethylamine (0.01 ml) was added to the solution, followed by stirring at room temperature for 24 hours. The reaction solvent was evaporated under reduced pressure and the residue was purified in the same manner as described in Example 6 to obtain 12 mg of 2-(2-acetamido-2,6-dideoxy-6-mycoloylamino-D-glucopyranos-3-O-yl)-D-propionyl-L-alanyl-D-isoglutamine as crystals. Melting point, 157°–160° C. (decomposition).

Elemental analysis for $C_{99}H_{189}N_5O_{12.5}$: Calcd.: C, 72.08; H, 11.55; N, 4.25. Found: C, 71.86; H, 11.63; N, 4.20.

EXAMPLE 8

Benzyl 2-(benzyl 2-acetamido-6-azido-2,6-dideoxy-α-D-glucopyranosid-3-O-yl)-D-propionyl-L-valyl-D-isoglutaminate (230 mg, 0.32 mmol) was hydrogenated in the same manner as described in Example 4 and thereafter the solvent was evaporated. The resulting residue was dissolved in DMF (6 ml), and stearic acid HOSuc ester (244 mg, 0.64 mmol) and triethylamine (0.05 ml) were added to the solution, followed by stirring at room temperature for 15 hours. The reaction solvent was evaporated under reduced pressure and the residue was purified in the same manner as described in Example 5 to obtain 85 mg of 2-(2-acetamido-2,6-dideoxy-6- stearoylamino-D-glucopyranos-3-O-yl)-D-propionyl-L-valyl-D-isoglutamine as crystals. Melting point, 167°–169° C. (decomposition). $[\alpha]_D^{19} +5.9°$ (after 24 hours; c 0.22, chloroform-methanol=1:1).

Elemental analysis for $C_{39}H_{71}N_5O_{11}$: Calcd.: C, 59.59; H, 9.11; N, 8.91. Found: C, 59.32; H, 9.40; H, 8.66.

EXAMPLE 9

Benzyl 2-(benzyl 2-acetamido-6-azido-2,6-dideoxy-α-D-glucopyranosid-3-O-yl)-D-propionyl-L-valyl-D-isoglutaminate (150 mg, 0.21 mmol) was hydrogenated in the same manner as described in Example 4 and thereafter the solvent was removed. The resulting residue was dissolved in DMF (3 ml), and mycolic acid HOSuc ester (450 mg, 0.36 mmol) dissolved in benzene (3 ml) and triethylamine (0.02 ml) were added to the solution, followed by stirring at room temperature for 24 hours. The reaction solvent was evaporated under reduced pressure and the residue was purified in the same manner as described in Example 6 to obtain 110 mg of 2-(2-acetamido-2,6-dideoxy-6-mycoloylamino-D-glucopyranos-3-O-yl)-D-propionyl-L-valyl-D-isoglutamine as crystals. Melting point 178°–180° C. (decomposition). $[\alpha]_D^{19} +15.0°$ (after 24 hours; c 0.20, chloroform-methanol=1:1).

Elemental analysis for $C_{101}H_{193}N_5O_{12.5}$: Calcd.: C, 72.24; H, 11.59; N, 4.17. Found: C, 72.18; H, 11.36; N, 4.08.

EXAMPLE 10

Benzyl 2-(benzyl 2-acetamido-6-azido-2,6-dideoxy-α-D-glucopyranosid-3-O-yl)-D-propionyl-O-benzyl-L-seryl-D-isoglutaminate (250 mg, 0.31 mmol) was hydrogenated in the same manner as described in Example 4 and thereafter the solvent was evaporated. The resulting residue was dissolved in a mixture of DMF (2 ml) and dioxane (3 ml), and nocardomycolic acid HOSuc ester (250 mg, 0.29 mmol) and triethylamine (0.05 ml) were added to the solution, followed by stirring at room temperature for 24 hours. The reaction solvent was distilled off under reduced pressure and the residue was purified in the same manner as described in Example 6 to obtain 50 mg of 2-(2-acetamido-2,6-dideoxy-6-nocardomycoloylamino-D-glucopyranos-3-O-yl)-D-propinyl-L-seryl-D-isoglutamine as crystals. Melting point, 144°–146° C. (decomposition). $[\alpha]_D^{24} +7.5°$ (after 24 hours; c 0.16, chloroform-methanol=1:1).

Elemental analysis for $C_{70}H_{128}N_5O_{13.6}$: Calcd.: C, 66.86; H, 10.26; N, 5.57. Found: C, 66.69; H, 10.31; N, 5.58.

EXAMPLE 11

(I) Benzyl 2-acetamido-2-dideoxy-6-O-mesyl-3-O-[D-1-(methoxycarbonyl)ethyl]-α-D-glucopyranoside (6.0 g, 12.2 mmol) was dissolved in anhydrous pyridine (20 ml). Then acetic anhydride (1.7 ml) was added to the solution and the mixture was allowed to stand overnight. After completion of the reaction, the reaction mixture was concentrated at 30° C. under reduced pressure. The residue was extracted with chloroform. The extract was then washed successively with 2 N hydrochloric acid, 1 N sodium carbonate and water, dryed over anhydrous sodium sulfate, and evaporated. The resulting syrup was crystallized from ethyl acetate-n-hexane to obtain 6.1 g of benzyl 2-acetamido-4-O-acetyl-2-deoxy-6-O-mesyl-3-O-[D-1-(methoxycarbonyl)ethyl]-α-D-glucopyranoside. Melting point, 144°–145° C. $[\alpha]_D^{22} +83°$ (c 1.0, chloroform).

Elemental analysis for $C_{22}H_{31}NO_{11}S$: Calcd.: C, 51.05; H, 6.04; N, 2.71; S, 6.20. Found: C, 50.88; H, 6.52; N, 2.78; S, 6.55.

(II) Benzyl 2-acetamido-4-O-acetyl-2-deoxy-6-O-mesyl-[D-1-(methoxycarbonyl)ethyl]-α-D-glucopyranoside (500 mg, 0.97 mmol) was dissolved in DMF (6 ml) and sodium azide was added to the solution, followed by heating at 60° C. for 5 hours with stirring. After completion of the reaction, the inorganic material was filtered using Celite and DMF was concentrated at 70° C. under reduced pressure. The residue was worked-up in the same manner as described in Example 11 (I) to obtain 410 mg of benzyl 2-acetamido-4-O-acetyl-6-azido-2,6-dideoxy-3-O-[D-1-(methoxycarbonyl)ethyl]-α-D-glucopyranoside as crystals. Melting point, 133°–134° C. $[\alpha]_D^{21} +88°$ (c, 0.7 in chloroform).

Elemental analysis for $C_{21}H_{28}H_4O_8$: Calcd.: C, 54.30; H, 6.08; N, 12.06. Found: C, 54.59; H, 5.92; N, 11.99.

(III) Benzyl 2-acetamido-4-O-acetyl-6-azido-2,6-dideoxy-3-O-[D-1-(methoxycarbonyl)ethyl]-α-D-glucopyranoside (500 mg, 1.08 mmol) was dissolved in ethanol (60 ml) and a 10% palladium-carbon catalyst (50 mg) pretreated with hydrogen was added to the solution, followed by hydrogenation for 1 hour. After completion of the reaction, the catalyst was filtered and the solvent was evaporated. The residue was dissolved in methanol (5 ml), and acetic anhydride (0.5 ml) was added. After completion of the reaction, the reaction solution was concentrated under reduced pressure and the resulting syrup was purified by column chromatography (Wakogel C-300, 10 g; chloroform-methanol=50:1 v/v) to obtain 430 mg of benzyl 3,6-diacetamido-4-O-acetyl-2,6-dideoxy-3-O-[D-1-(methoxycarbonyl)ethyl]-α-D-glucopyranoside.

Melting point, 223°–224° C. $[\alpha]_D^{21} +114°$ (c 0.7, chloroform).

Elemental analysis for $C_{23}H_{32}N_2O_9$: Calcd.: C, 57.49; H, 6.71; N, 5.83. Found: C, 57.26; H, 6.81; N, 5.90.

(IV) Benzyl 2,6-diacetamido-4-O-acetyl-2,6-dideoxy-3-O-[D-1-(methoxycarbonyl)ethyl]-α-D-glucopyranoside (500 mg, 1.04 mmol) was dissolved in methanol (10 ml), and sodium metal (50 mg) was added to the solution, followed by stirring at room temperature. After the starting material disappeared, water (10 ml) was added to the mixture and the stirring was continued. After completion of the reaction, the reaction mixture was neutralized with Amberlite IR-120 (H+) and, after the resin was removed by filtration, the solvent was evaporated to obtain 440 mg of benzyl 2,6-diacetamido-3-O-(D-1-carboxyethyl)-2,6-2,6-dideoxy-α-D-glucopyranoside. $[\alpha]_D^{21} +64°$ (c. 0.4, methanol).

Elemental analysis for $C_{20}H_{28}N_2O_8$: Calcd.: C, 56.59; H, 6.65; N, 6.60. Found: C, 56.82; H, 6.33; N, 6.82.

(V) Benzyl 2,6-diacetamido-3-O-(D-1-carboxyethyl)-2,6-dideoxy-α-D-glucopyranoside (400 mg, 0.94 mmol) was dissolved in DMF (10 ml), and DCC (320 mg, 1.55 mmol) and N-hydroxysuccinimide were added to the solution, followed by stirring at room temperature for 1 hour. After completion of the reaction, L-alanyl-D-isoglutamine benzyl ester trifluoroacetate (650 mg) and triethylamine (120 mg) were added to the reaction mixture, followed by stirring at 0° C. After 3 hours, the precipitate was filtered using Celite, and the filtrate was concentrated at a low temperature under reduced pressure. The residue was subjected to silica gel column chromatography and the column was eluted first with chloroform and then chloroform-methanol (50:1 v/v), whereby 600 mg of benzyl 2-(benzyl 2,6-diacetamido- 2,6-dideoxy-α-D-glucopyranosid-3-O-yl)-D-propionyl-L-alanyl-D-isoglutaminate was obtained from the chloroform-methanol eluate. $[\alpha]_D^{21} +73°$ (c 0.77, DMF).

Elemental analysis for $C_{35}H_{47}N_5O_{11}$: Calcd.: C, 58.89; H, 6.65; N, 9.81. Found: C, 59.23; H, 6.14; N, 10.19.

EXAMPLE 12

(I) Methyl 2-(benzyl 2-acetamido-2-deoxy-α-D-glucopyranosid-3-O-yl)-D-propionyl-L-valyl-D-isoglutaminate (624.7 mg, 1 mmol) was dissolved in a mixture of pyridine (45 ml) and tetrahydrofuran (20 ml), and p-toluenesulfonyl chloride (2.29 g, 12 mmol) was added while cooling with ice. After stirring for 2 hours under ice-cooling, additional p-toluenesulfonyl chloride (2.29 g, 12 mmol) was added. The mixture was allowed to react for 30 minutes under ice-cooling and then for 1 hour at room temperature, and ice-water (30 ml) was added to the reaction solution, followed by stirring for 30 minutes. The solvent was evaporated, the residue was dissolved in ethyl acetate (30 ml) and the solution was washed successively with a 5% sodium bicarbonate solution, 1 N hydrochloric acid and water. The solution was dried over anhydrous sodium sulfate, and ethyl acetate was evaporated. Diethyl ether was added to the residue, and the precipitate was separated by filtration and recrystallized from ethanoldiethyl ether to obtain methyl 2-(benzyl 2-acetamido-2-deoxy-6-O-tosyl-α-D-glucopyranosid-3-O-yl)-D-propionyl-L-valyl-D-isoglutaminate (480 mg). Melting point, 178°–180° C. $[\alpha]_D^{21} +91.9°$ (c 0.5, DMF). $Rf^1 = 0.60$, $Rf^2 = 0.09$.

Elemental analysis for $C_{36}H_{50}N_4O_{13}S$: Calcd.: C, 55.51; H, 6.47; N, 7.19; S, 4.12. Found: C, 55.31; H, 6.45; N, 7.05; S, 4.15.

(II) Methyl 2-(benzyl 2-acetamido-2-deoxy-6-O-tosyl-α-D-glucopyranosid-3-O-yl)-D-propionyl-L-valyl-D-isoglutaminate (421 mg, 0.54 mmol) was dissolved in anhydrous DMF (1.5 ml), and sodium azide (351 mg, 5.4 mmol) was added to the solution. After reaction at 80° C. for 4 hours, water (1 ml) was added. The solvent was evaporated and the residue was dissolved in a mixture of chloroform (25 ml) and n-butanol (5 ml). The solution was washed three times with a small amount of water, dried over anhydrous sodium sulfate and evaporated. The crystalline residue was washed with hot ethyl acetate to obtain methyl 2-(benzyl 2-acetamido-6-azido-2,6-dideoxy-α-D-glucopyranosid-3-O-yl)-D-propionyl-L-valyl-D-isoglutaminate (329 mg).

Melting point, 213°–214° C. $[\alpha]_D^{21} +100.0°$ (c, 0.5, DMF). $Rf^1 = 0.48$, $Rf^3 = 0.56$ Elemental analysis for $C_{29}H_{43}N_7O_{10}$: Calcd.: C, 53.61; H, 6.67; N, 15.09. Found: C, 53.47; H, 6.59; N, 14.73.

(III) Methyl 2-(benzyl 2-acetamido-6-azido-2,6-dideoxy-α-D-glucopyranosid-3-O-yl)-D-propionyl-L-valyl-D-isoglutaminate (267 mg, 0.41 mmol) was dissolved in methanol (10 ml)-1 N hydrochloric acid (0.41 ml) and hydrogenated at room temperature for 3 hours in the presence of palladium black as a catalyst. The catalyst was filtered and the solvent was evaporated. The residue was dissolved in a small amount of methanol and diethyl ether was added. The precipitate was filtered to obtain methyl 2-(2-acetamido-6-amino-2,6-dideoxy-D-glucopyranos-3-O-yl)-D-propionyl-L-valyl-D-isoglutaminate hydrochloride (255 mg). Melting point, 162° C. (decomposition). $[\alpha]_D^{22} +57.5°$ (c 0.5, DMF). $Rf^4 = 0.07$, $Rf^5 = 0.48$.

Elemental analysis for $C_{22}H_{39}N_5O_{10}\cdot HCl\cdot H_2O$: Calcd.: C, 44.93; H, 7.20; N, 11.91; Cl, 6.03. Found: C, 45.16; H, 7.66; N, 11.63; Cl, 6.04.

EXAMPLE 13

Methyl 2-(2-acetamido-6-amino-2,6-dideoxy-D-glucopyranos-3-O-yl)-D-propionyl-L-valyl-D-isoglutaminate hydrochloride (45.6 mg, 0.08 mmol) and 10-(2,3-dimethoxy-5-methyl-1,4-bzneoquinon-6-yl)decanoic acid p-nitrophenyl ester (42.6 mg, 0.09 mmol) were dissolved in DMF (0.4 ml), and N-ethylmorpholine (0.012 ml) was added to the solution. After the mixture was allowed to react for 15 hours, the solvent was evaporated, and the residue was purified by column chromatography on silica gel (column size: 1.5 cmφ × 12 cm; the elution solvent was the same solvent system as used for $Rf^1$. The fractions containing the pure desired compound were collected and the solvent was evaporated. The residue was further purified by column chromatography on Sephadex LH-20 (column size: 1.5 cmφ × 45 cm; elution solvent: ethanol-0.1 N acetic acid = 3:2 v/v). The fractions containing the desired compound were collected and the solvent was evaporated. The crystalline residue thus obtained was recrystallized from ethanol-diethyl ether to obtain methyl 2-{2-acetamido-2,6-dideoxy-6-[10-(2,3-dimethoxy-5-methyl-1,4-benzoquinon-6-yl)decanoyl]amino-D-glucopyranos-3-O-yl}-D-propionyl-L-valyl-D-isoglutaminate (42.1 mg). Melting point, 206°–208° C. (decomposition). $[\alpha]_D^{21} +23.3°$ (c 0.3, ethanol). $Rf^1 = 0.39$, $Rf^3 = 0.33$, $Rf^4 = 0.77$.

Elemental analysis for $C_{41}H_{65}N_5O_{15}\cdot\frac{1}{2}H_2O$: Calcd.: C, 56.14; H, 7.59; N, 7.99. Found: C, 56.28; H, 7.46; N, 7.65.

EXAMPLE 14

6-(2,3,5-Trimethyl-1,4-benzoquinon-6-yl)-4-methylhexanoic acid (29.2 mg, 0.1 mmol) and p-nitrophenol (16.0 mg, 0.115 mmol) were dissolved in ethyl acetate (0.5 ml), followed by cooling with ice. To the solution was added DCC (23.7 mg, 0.115 mmol) and the mixture was allowed to react for 2 hours under ice-cooling and then at room temperature for 13 hours. The precipitate was filtered and the solvent was evaporated. The residue was dissolved in DMF (0.5 ml) together with methyl 2-(2-acetamido-6-amino-2,6-dideoxy-D-glucopyranos-3-O-yl)-D-propionyl-L-valyl-D-isoglutaminate hydrochloride (45.6 mg, 0.09 mmol) and N-ethylmorpholine (12 μl), and the mixture was allowed to react for 15 hours at room temperature. The solvent was evaporated, and the residue was worked-up and purified in the same manner as described in Example 13 to obtain methyl 2-{2-acetamido-2,6-dideoxy-6-[6-(2,3,5-trimethyl-1,4-benzoquinon-6-yl)-4-methylhexanoyl]amino-D-glucopyranos-3-O-yl}-D-propionyl-L-valyl-D-isoglutaminate (30 mg). Melting point, 192° C. (decomposition). $[\alpha]_D^{22} +34.2°$ (c 0.4, methanol). $Rf^1 = 0.42$, $Rf^3 = 0.37$, $Rf^4 = 0.78$.

Elemental analysis for $C_{38}H_{59}N_5O_{13}$: Calcd.: C, 57.48; H, 7.49; N, 8.82. Found: C, 57.19; H, 7.48; N, 8.63.

EXAMPLE 15

9-(2-methyl-1,4-naphthoquinon-3-yl)nonanoic acid (32.8 mg, 0.1 mmol) and p-nitrophenol (16.0 mg, 0.115 mmol) were dissolved in ethyl acetate (2 ml), followed by ice-cooling. To the solution was added DCC (23.7 mg, 0.115 mmol) and the mixture was allowed to react for 2 hours under ice-cooling and for 13 hours at room temperature. The precipitate was filtered and the solvent was evaporated. The residue was dissolved in DMF (0.3 ml) together with methyl 2-(2-acetamido-6-amino-2,6-dideoxy-D-glucopyranos-3-O-yl)-D-propionyl-L-valyl-D-isoglutaminate hydrochloride (45.6 mg, 0.09 mmol) and N-ethylmorpholine (12 μl), and the mixture was allowed to react for 15 hours at room temperature. The solvent was removed, and the residue was purified in the same manner as described in Example 13 to obtain methyl 2-{2-acetamido-2,6-dideoxy-6-[9-(2-methyl-1,4-naphthoquinon-3-yl)nonanoyl]amino-D-glucopyranos-3-O-yl}-D-propinyl-L-valyl-D-isoglutaminate (22 mg). Melting point 213° C. (decomposition). $[\alpha]_D^{22}+24.9°$ (c 0.4, methanol). $Rf^1=0.49$, $Rf^3=0.38$, $Rf^4=0.83$.

Elemental analysis for $C_{42}H_{61}N_5O_{13}$: Calcd.: C, 59.77; H, 7.29; N, 8.30. Found: C, 59.42; H, 7.24; N, 8.24.

EXAMPLE 16

(I) Isopropyl t-butyloxycarbonyl-D-isoglutaminate (176 mg, 0.61 mmol) was treated with trifluoroacetic acid (1 ml) at room temperature for 20 minutes. Trifluoroacetic acid was evaporated and the residue was washed thoroughly with a mixture of diethyl ether-petroleum ether (1:1) and dried in a desiccator over sodium hydroxide pellets. The resulting trifluoroacetic acid salt was dissolved in acetonitrile (10 ml) together with triethylamine (0.19 ml). To this solution was added t-butyloxycarbonyl-O-benzyl-L-serine HOSuc ester (274 mg, 0.7 mmol), and the mixture was allowed to react for 15 hours at room temperature. The solvent was evaporated and the residue was dissolved in ethyl acetate (20 ml). The solution was washed successively with a 5% aqueous sodium bicarbonate solution, 1 N hydrochloric acid and water, dried over anhydrous sodium sulfate, and evaporated. The residue was crystallized by addition of petroleum ether and the resulting crystals were filtered to obtain isopropyl t-butyloxycarbonyl-O-benzyl-L-seryl-D-isoglutaminate (243 mg). Melting point, 98°–99° C. $[\alpha]_D^{22}+2.0°$ (c 0.5, DMF). $Rf^2=0.50$; $Rf^3=0.78$.

Elemental analysis for $C_{23}H_{35}N_3O_7$: Calcd.: C, 59.34; H, 7.58; N, 9.03. Found: C, 59.20; H, 7.62; N, 9.03.

(II) Isopropyl t-butyloxycarbonyl-O-benzyl-L-seryl-D-isoglutaminate (233 mg, 0.48 mmol) was treated with trifluoroacetic acid (1.5 ml) at room temperature for 20 minutes in the same manner as described in Example 16 (I). The resulting trifluoroacetic acid salt, triethylamine (0.1 ml) and 2-(benzyl 2-acetamido-4,6-O-benzylidene-2-deoxy-α-D-glucopyranosid-3-O-yl)-D-propionic acid N-hydroxy-5-norbornene-2,3-dicarboximide ester (316 mg, 0.5 mmol) were dissolved in acetonitrile (10 ml). The solution was allowed to react at room temperature for 60 hours and cooled. The precipitated crystals were filtered to obtain isopropyl 2-(benzyl 2-acetamido-4,6-O-benzylidene-2-deoxy-α-D-glucopyranosid-3-O-yl)-D-propionyl-O-benzyl-L-seryl-D-isoglutaminate (383 mg). Melting point, higher than 240° C. $[\alpha]_D^{24}+74.9°$ (c 0.5, DMF). $Rf^1=0.72$; $Rf^2=0.38$; $Rf^3=0.78$.

Elemental analysis for $C_{43}H_{54}N_4O_{12}.H_2O$: Calcd.: C, 61.71; H, 6.75; N, 6.69. Found: C, 61.89; H, 6.80; N, 6.99.

(III) Isopropyl 2-(benzyl 2-acetamido-4,6-O-benzylidene-2-deoxy-α-D-glucopyranosid-3-O-yl)-D-propionyl-O-benzyl-L-seryl-D-glutaminate (360 mg, 0.44 mmol) was dissolved in 75% acetic acid (20 ml) and the solution was heated at 100° C. for 20 minutes. The solvent was evaporated. After flushing twice with water, and then twice with toluene, the crystalline residue was recrystallized from methanoldiethyl ether to obtain isopropyl 2-(benzyl 2-acetamido-2-deoxy-α-D-glucopyranosid-3-O-yl)-D-propionyl-O-benzyl-L-seryl-D-isoglutaminate (240 mg). Melting point, 220° C. $[\alpha]_D^{22}+93.0°$ (c 0.5, DMF). $Rf^1=0.47$, $Rf^3=0.36$.

Elemental analysis for $C_{36}H_{50}N_4O_{12}.\frac{1}{2}H_2O$: Calcd.: C, 58.47; H, 7.09; N, 7.58. Found: C, 58.48; H, 6.92; N, 7.47.

(IV) Isopropyl 2-(benzyl 2-acetamido-2-deoxy-α-D-glucopyranosid-3-O-yl)-D-propionyl-O-benzyl-L-seryl-D-isoglutaminate (220 mg, 0.3 mmol) was dissolved in pyridine (15 ml) and p-toluenesulfonyl chloride (1.14 g, 6 mmol) was added to the solution while cooling with ice. After 40 minutes, an additional amount of the same reagent (0.6 g, 3 mmol) was added, and the mixture was allowed to react for 1 hour under ice-cooling, followed by addition of ice-water (5 ml). The mixture was worked-up and purified in the same manner as described in Example 12-(I) to obtain isopropyl 2-(benzyl 2-acetamido-2-deoxy-6-O-tosyl-α-D-glucopyranosid-3-O-yl)-D-propionyl-O-benzyl-L-seryl-D-isoglutaminate (192 mg). Melting point, 178°–179° C. $[\alpha]_D^{22}+76.2°$ (c 0.5, DMF) $Rf^1=0.60$, $Rf^2=0.14$, $Rf^3=0.63$.

Elemental analysis for $C_{43}H_{56}N_4O_{14}S$: Calcd.: C, 58.35; H, 6.38; N, 6.33. Found: C, 58.11; H, 6.30; N, 6.25.

(V) Isopropyl 2-(benzyl 2-acetamido-2-deoxy-6-O-tosyl-α-D-glucopyranosid-3-O-yl)-D-propionyl-O-benzyl-L-seryl-D-isoglutaminate (120 mg, 0.19 mmol) was dissolved in anhydrous DMF (1 ml) and sodium azide (123 mg, 1.9 mmol was added to the solution. The mixture was allowed to react for 3 hours at 80° C., and the solvent was evaporated. The residue was then worked-up and purified in the same manner as described in Example 12-(II) to obtain isopropyl 2-(benzyl 2-acetamido-6-azido-2,6-dideoxy-α-D-glucopyranosid-3-O-yl)-D-propionyl-O-benzyl-L-seryl-D-isoglutaminate (135 mg). Melting point, 222°–224° C. (decomposition). $[\alpha]_D^{22}+87.5°$ (c 0.5, DMF). $Rf^1=0.60$, $Rf^3=0.56$.

Elemental analysis for $C_{36}H_{49}N_7O_{11}$: Calcd.: C, 57.20; H, 6.53; N, 12.97. Found: C, 57.19; H, 6.54; N, 12.66.

(VI) Isopropyl 2-(benzyl 2-acetamido-6-azido-2,6-dideoxy-α-D-glucopyranosid-3-O-yl)-D-propionyl-O-benzyl-L-seryl-D-isoglutaminate (115 mg, 0.152 mmol) was hydrogenated in acetic acid (5 ml)—isopropyl alcohol (2 ml) in the presence of palladium black as a catalyst at room temperature for 7 hours. The reaction mixture was worked-up and purified in the same manner as described in Example 12-(III) to obtain isopropyl 2-(2-acetamido-6-amino-2,6-dideoxy-D-glucopyranos-3-O-yl)-D-propionyl-L-seryl-D-isoglutaminate acetate (70.0 mg.). Melting point, 118° C. $[\alpha]_D^{22}+48.5°$ (c 0.5, DMF). $Rf^4=0.08$, $Rf^5=0.45$.

Elemental analysis for $C_{22}H_{39}N_5O_{11}.CH_3COOH.\frac{1}{2}H_2O$: Calcd.: C, 46.59; H, 7.17; N, 11.32. Found: C, 46.53; H, 7.17; N, 10.74.

EXAMPLE 17

Isopropyl 2-(2-acetamido-6-amino-2,6-dideoxy-D-glucopyranos-3-O-yl)-D-propionyl-L-seryl-D-isoglutaminate acetate (47.6 mg, 0.078 mmol) and 10-(2,3-dimethoxy-5-methyl-1,4-benzoquinon-6-yl)decanoic acid p-nitrophenyl ester (37.0 mg, 0.078 mmol) were dissolved in DMF (0.5 ml) together with N-ethylmorpholine (20 μl), and the mixture was allowed to react for 15 hours at room temperature. The reaction mixture was then worked-up and purified in the same manner as described in Example 13 to obtain isopropyl 2-{2- acetamido-2,6-dideoxy-6-[10-(2,3-dimethoxy-5-methyl-1,4-benzoquinon-6-yl)decanoyl]amino-D-glucopyranos-3-O-yl}-D-propionyl-L-seryl-D-isoglutaminate (37 mg). Melting point, 199° C. $[\alpha]_D^{22}+21.0°$ (c 0.4, methanol). $Rf^1=0.20$, $Rf^3=0.14$, $Rf^4=0.70$.

Elemental analysis for $C_{41}H_{65}N_5O_{16}$: Calcd.: C, 55.70; H, 7.41; N, 7.92. Found: C, 55.48; H, 7.36; N, 7.84. For the brevity of description, the following abbreviations are used after example 18.

10-(2,3-Dimethoxy-5-methyl-1,4-benzoquinon-6-yl)decanoyl; 10-(2,3,5-trimethyl-1,4-benzoquinon-6-yl)decanoyl; 3-(2,3-dimethoxy-5-methyl-1,4-benzoquinon-6-yl)propyonyl-; 9-(2-methyl-1,4-naphthoquinon-3-yl)nonanoyl; stearoyl; farnesylacetyl; benzyloxycarbonyl; and t-butyloxycarbonyl groups are designated as QS-10, ES-10, QS-3, KS-9, St, Far, Z and BOC, respectively. The developing solvent systems used hereinafter are shown by the following abbreviations:

$Rf^1$ = chloroform:methanol:acetic acid = 18:2:1, v/v
$Rf^2$ = ethyl acetate:pyridine:water:acetic acid = 30:10:5:3, v/v
$Rf^3$ = chloroform:methanol = 19:1, v/v
$Rf^4$ = chloroform:acetone:methanol = 10:3:2, v/v
$Rf^5$ = ethyl acetate:acetic acid:n-butanol:water = 1:1:1:1, v/v The term "$Rf^3=0.76$", for example, means that the compound has a Rf value of 0.76 on a silica gel plate developed with the $Rf^3$ solvent system described above.

EXAMPLE 18

In 96% ethanol (200 ml) were dissolved benzyl 2-acetamido-2-deoxy-4,6-O-isopropylidene-α-D-glucopyranoside (14.1 g, 40 mmol) and potassium hydroxide (60 g), and the solution was refluxed with stirring in an oil bath at 120° C. for 4 hours. The solvent was evaporated, the residue was diluted with water (300 ml) and the oily precipitate was extracted with chloroform (100 ml×3). The chloroform layers were combined, washed with water, dried over anhydrous sodium sulfate and evaporated. The crystalline residue was treated with ether and filtered. Recrystallization from methanol-ethyl ether gave 8.15 g of benzyl 2-amino-2-deoxy-4,6-O-isopropylidene-α-D-glucopyranoside, m.p. 142°-143° C., $[\alpha]_D^{25}+119.5°$ (c 0.5, chloroform), $Rf^1=0.39$, $Rf^2=0.51$.

Elemental analysis for $C_{16}H_{23}NO_5$: Calcd.: C, 62.12; H, 7.49; N, 4.53. Found: C, 62.29; H, 7.30; N, 4.58.

EXAMPLE 19

In tetrahydrofuran (50 ml) were dissolved benzyl 2-amino-2-deoxy-4,6-O-isopropylidene-α-D-glucopyranoside (8.1 g, 26.2 mmol), S-t-butyloxycarbonyl-4,6-dimethyl-2-mercaptopyrimidine (7.54 g, 31.4 mmol) and triethylamine (2.2 ml), and the reaction is carried out at room temperature for 24 hours and further in an oil bath at 60° C. for 15 hours. After evaporation, the residue was dissolved in ethyl acetate (150 ml). The solution was washed with cold 0.3 N hydrochloric acid and then water, dried over anhydrous sodium sulfate, and evaporated. The residue was purified by silica gel (200 g) column chromatography (column size: 4×25 cm). The column was washed with a 99:1 (v/v) mixture of chloroform and methanol and, then, eluted with a 49:1 (v/v) mixture of chloroform and methanol. The fractions containing the desired product were combined and the solvent was evaporated. The residue was crystallized from ethyl ether-petroleum ether to give 8.03 g of benzyl 2-t-butyloxycarbonylamino-2-deoxy-4,6-O-isopropylidene-α-D-glucopyranoside, m.p. 69°-70° C., $[\alpha]_D^{25}+99.8°$ (c 0.5, chloroform), $Rf^1=0.79$, $Rf^3=0.65$ Elemental analysis for $C_{21}H_{31}NO_7$: Calcd.: C, 61.56; H, 7.63; N, 3.42. Found: C, 61.26; H, 7.53; N, 3.77.

EXAMPLE 20

In anhydrous dioxane (100 ml) was dissolved benzyl 2-t-butyloxycarbonylamino-2-deoxy-4,6-O-isopropylidene-α-D-glucopyranoside (8.0 g, 19.5 mmol), and at a temperature not exceeding 40° C., sodium hydride (oil emulsion, 60% content) was added to the solution under nitrogen. Then, L-α-chloropropionic acid (5.31 g, 48.8 mmol) was added carefully in small portions. The reaction was conducted at room temperature for 15 hours and then water (30 ml) was added to the mixture with caution. The reaction mixture was adjusted to pH 7 with a 10% aqueous solution of citric acid. After concentration, the residual aqueous solution was cooled and adjusted to pH 3 with a 10% aqueous solution of citric acid. The resulting oily precipitate was extracted with ethyl ether (300 ml) and the ethereal layer was washed with water, dried over anhydrous sodium sulfate, and evaporated to give 8.10 g of 2-(benzyl-2-t-butyloxycarbonylamino-2-deoxy-4,6-O-isopropylidene-α-D-glucopyranosid-3-O-yl)-D-propionic acid as an oil. A small portion of this oil (190 mg, 0.4 mmol) was dissolved in a small amount of ethyl ether and, then, dicyclohexylamine (0.08 ml, 0.4 mmol) was added. The solvent was evaporated and the residue was crystallized by the addition of petroleum ether. The desired dicyclohexylamine salt thus obtained was served as an analytical sample. m.p. 107°-108° C., $[\alpha]_D^{22}+73.4°$ (c 0.5, DMF), $RF^1=0.72$.

Elemental analysis for $C_{36}H_{58}N_2O_9$: Calcd.: C, 65.23; H, 8.82; N, 4.23. Found: C, 64.94; H, 8.93; N, 4.18.

EXAMPLE 21

In acetonitrile (50 ml) were dissolved 2-(benzyl 2-t-butyloxycarbonylamino-2-deoxy-4,6-O-isopropylidene-α-D-glucopyranoside (oil, 8.10 g, 16.8 mmol) and N-hydroxy-5-norbornene-2,3-dicarboximide (3.01 g, 16.8 mmol). Under ice-cooling, dicyclohexylcarbodiimide (3.46 g, 16.8 mmol) was added and the mixture was stirred under ice cooling for 2 hours and at room temperature for 15 hours. After filtration and evaporation, the residue was dissolved in ethyl acetate (100 ml). The solution was washed with a 5% aqueous solution of sodium hydrogen carbonate and then water, dried over anhydrous sodium sulfate, and evaporated to give 10.8 g of the N-hydroxy-5-norbornene-2,3-dicarboximide ester, an active ester, of 2-(benzyl 2-t-butyloxycarbonylamino-2-deoxy-4,6-O-isopropylidene-α-D-glucopyranosid-3-O-yl)-D-propionic acid (oil, $Rf^3=0.74$).

On the other hand, methyl benzyloxycarbonyl-L-valyl-D-isoglutaminate (3.62 g, 9.2 mmol) and p-toluene sulfonic acid (1.75 g, 9.2 mmol) were dissolved in N,N-dimethylformamide (50 ml) and the catalytic hydrogenation was carried out with palladium black as a catalyst at room temperature for 4 hours. After filtration and evaporation of the solvent, the residue was dissolved in acetonitrile (50 ml) together with the active ester previously obtained (5.92 g, 9.2 mmol), followed by the addition of triethylamine (1.29 ml) under ice-cooling. After reaction at room temperature for 60 hours, the solvent was evaporated. The residue was dissolved in ethyl acetate (100 ml), the insolubles were filtered and the filtrate was washed with 20% acetic acid, 5% aqueous sodium hydrogen carbonate and water successively, and dried over anhydrous sodium sulfate. The solvent was evaporated and the residue was crystallized by the addition of petroleum ether. Recrystallization from ethyl acetate-petroleum ether gave 3.35 g of methyl 2-(benzyl 2-t-butyloxycarbonylamino-2-deoxy-4,6-O-isopropylidene-α-D-glucopyranosid-3-O-yl)-D-propionyl-L-valyl-D-isoglutaminate. m.p. 141°–142° C., $[\alpha]_D^{22}+103.5°$ (c 0.5, N,N-dimethylformamide), $Rf^1=0.79$, $Rf^3=0.26$, $Rf^4=0.71$.

Elemental analysis for $C_{35}H_{54}N_4O_{12}$: Calcd.: C, 58.15; H, 7.53; N, 7.75. Found: C, 57.94; H, 7.55; N, 7.78.

EXAMPLE 22

In 75% acetic acid (20 ml) was dissolved methyl 2-(benzyl 2-t-butyloxycarbonylamino-2-deoxy-4,6-O-isopropylidene-α-D-glucopyranosid-3-O-yl)-D-propionyl-L-valyl-D-isoglutaminate (3.32 g, 4.59 mmol), and the reaction was carried out at room temperature for 3 hours. The solvent was evaporated at a temperature not exceeding 40° C. The residue was flushed with toluene and recrystallized from methanol-ethyl ether-petroleum ether to give 3.05 g of methyl 2-(benzyl 2-t-butyloxycarbonylamino-2-deoxy-α-D-glucopyranosid-3-O-yl)-D-propionyl-L-valyl-D-isoglutaminate. m.p. 186° C., $[\alpha]_D^{22}+98.0°$ (c 0.5, N,N-dimethylformamide), $Rf^1=0.54$, $Rf^4=0.38$.

Elemental analysis for $C_{32}H_{50}N_4O_{12}$: Calcd.: C, 56.29; H, 7.38; N, 8.21. Found: C, 56.32; H, 7.32; N, 8.23.

EXAMPLE 23

Methyl 2-(benzyl 2-t-butyloxycarbonylamino-2-deoxy-α-D-glucopyranosid-3-O-yl)-D-propionyl-L-valyl-D-isoglutaminate (3.00 g, 4.39 mmol) was dissolved in pyridine (25 ml) and the solution was cooled with ice. To this solution was added p-toluenesulfonyl chloride and, under ice-cooling, the reaction was conducted for 30 minutes. To this reaction mixture was added a further amount (1.68 g, 8.78 mmol) of p-toluenesulfonyl chloride and after an hour of reaction, a small amount of ice-water was added and the solvent was evaporated. The residue was dissolved in ethyl acetate (50 ml) and the solution was washed with water (20 ml). The water layer was extracted again with ethyl acetate (20 ml) and the ethyl acetate layers were combined, washed with 5% aqueous sodium hydrogen carbonate, 1 N hydrochloric acid and water successively, dried over anhydrous sodium sulfate, and evaporated. The residue was crystallized by the addition of ethyl ether. A small amount of petroleum ether was further added. After cooling, the crystals were filtered to give 3.32 g of methyl 2-(benzyl 2-t-butyloxycarbonylamino-2-deoxy-6-O-p-toluenesulfonyl-α-D-glucopyranosid-3-O-yl)-D-propionyl-L-valyl-D-isoglutaminate. m.p. 136°–139° C., $[\alpha]_D^{22}+84.1°$ (c 0.5, N,N-dimethylformamide), $Rf^1=0.70$, $Rf^3=0.50$, $Rf^4=0.70$.

Elemental analysis for $C_{39}H_{56}N_4O_{14}S$: Calcd.: C, 55.96; H, 6.74; N, 6.69; S, 3.83. Found: C, 55.79; H, 6.80; N, 6.80; S, 3.76.

EXAMPLE 24

Methyl 2-(benzyl 2-t-butyloxycarbonylamino-2-deoxy-6-O-p-toluenesulfonyl-α-D-glucopyranosid-3-O-yl)-D-propionyl-L-valyl-D-isoglutaminate (3.28 g, 3.92 mmol) and sodium azide (2.55 g, 39.2 mmol) were reacted in anhydrous N,N-dimethylformamide (20 ml) at 80° C. for 3 hours. The solvent was evaporated and the residue was extracted with ethyl acetate-water (50 ml-10 ml). The ethyl acetate layer was separated and the water layer was extracted again with ethyl acetate (20 ml). The ethyl acetate layers were combined, washed three times with a small amount of water, dried over anhydrous sodium sulfate, and evaporated. The residue was crystallized from ethyl ether to give 2.00 g of methyl 2-(benzyl 6-azido-2-t-butyloxycarbonylamino-2,6-dideoxy-α-D-glucopyranosid-3-O-yl)-D-propionyl-L-valyl-D-isoglutaminate. m.p. 140°–141° C., $[\alpha]_D^{22}+86.7°$ (c 0.5, N,N-dimethylformamide), $Rf^1=0.70$, $Rf^3=0.17$, $Rf^4=0.71$.

Elemental analysis for $C_{32}H_{49}N_7O_{11}$: Calcd.: C, 54.30; H, 6.98; N, 13.85. Found: C, 54.31; H, 7.01; N, 13.64.

EXAMPLE 25

Methyl 2-(benzyl 6-azido-2-t-butyloxycarbonylamino-2,6-dideoxy-α-D-glucopyranosid-3-O-yl)-D-propionyl-L-valyl-D-isoglutaminate (1.97 g, 2.78 mmol) was catalytically hydrogenated in methanol-acetic acid (10 ml-10 ml) at room temperature for 6 hours with palladium black as a catalyst. The catalyst was filtered, the solvent was evaporated and the residue was flushed with toluene. A 1:1 mixture of ethyl ether-petroleum ether was added to the residue and the solid precipitate was filtered to give 1.76 g of methyl 2-(6-amino-2-t-butyloxycarbonylamino-2,6-dideoxy-D-glucopyranos-3-O-yl)-D-propionyl-L-valyl-D-isoglutaminate acetate. m.p. 101°–103° C., $[\alpha]_D^{22}+43.0°$ (c 0.5, N,N-dimethylformamide), $Rf^2=0.36$.

Elemental analysis for $C_{25}H_{45}N_5O_{11}\cdot CH_3COOH$: Calcd.: C, 49.76; H, 7.58; N, 10.74. Found: C, 49.79; H, 7.94; N, 10.64.

EXAMPLE 26

In N,N-dimethylformamide (5 ml) were dissolved methyl 2-(6-amino-2-t-butyloxycarbonylamino-2,6-dideoxy-D-glucopyranos-3-O-yl)-D-propionyl-L-valyl-D-isoglutaminate acetate (657 mg, 1 mmol) and p-nitrophenyl 10-(2,3-dimethoxy-5-methyl-1,4-benzoquinon-6-yl)decanoate (710 mg, 15 mmol), together with N-ethylmorpholine (0.26 ml) and the reaction was carried out at room temperature for 24 hours. The solvent was evaporated and the residue was dissolved in a small amount of chloroform and purified by silica gel thin-layer chromatography (Merck, 20×20 cm). Thus, the thin-layer plate given the sample was developed with a 10:3:2 mixture of chloroform, acetone and methanol and the silica gel corresponding to the desired compound was scraped off and extracted with methanol. The methanol was distilled off and the residue was dissolved in ethyl acetate. The solution was washed with water, dried over anhydrous sodium sulfate, and evaporated. Then, ethyl ether was added to the residue and the solid precipitate was filtered to give 570 mg of methyl 2-(2-t-butyloxycarbonylamino-2,6-dideoxy-6-{10(2,3-dimethoxy-5-methyl-1,4-benzoquinon-6-yl)decanoyl}amino-D-glucopyranos-3-O-yl]-D-propionyl-L-valyl-D-isoglutaminate. m.p. 92°–94° C., $[\alpha]_D^{22}+23.1°$ (c 0.5, ethanol), $Rf^1=0.63$, $Rf^4=0.60$.

Elemental analysis for $C_{44}H_{71}N_5O_{16}$: Calcd.: C, 57.06; H, 7.73; N, 7.56. Found: C, 57.07; H, 7.94; N, 7.64.

EXAMPLE 27

In dioxane (1 ml) was dissolved methyl 2-[2-t-butyloxycarbonylamino-2,6-dideoxy-6-{10-(2,3-dime- TABLE 2-continued

| Compd. No. | X | M | R² | R³ | R⁴ | R⁶ | R⁵ | R | R⁷ |
|---|---|---|---|---|---|---|---|---|---|
| 11 | NH₂ | H | CH₃ | (CH₃)₂CH | H | $\overset{O}{\underset{\|}{C}}OH$ | CONH₂ | Boc | H |
| 12 | H, QS-10-N | H | CH₃ | (CH₃)₂CH | H | $\overset{O}{\underset{\|}{C}}OH$ | CONH₂ | Boc | H |
| 13 | H, QS-10-N | H | CH₃ | (CH₃)₂CH | H | $\overset{O}{\underset{\|}{C}}OH$ | CONH₂ | H | H |
| 14 | H, QS-10-N | H | CH₃ | (CH₃)₂CH | H | $\overset{O}{\underset{\|}{C}}OH$ | CONH₂ | QS-10 | H |
| 15 | C₆H₅CH(O—) | | CH₃ | C₆H₅CH₂OCH₂ | H | $\overset{O}{\underset{\|}{C}}OCH_3$ | CONH₂ | Boc | C₆H₅CH₂ |
| 16 | OH | H | CH₃ | C₆H₅CH₂OCH₂ | H | $\overset{O}{\underset{\|}{C}}OCH_3$ | CONH₂ | Boc | C₆H₅CH₂ |
| 17 | p-CH₃C₆H₅SO₃ | H | CH₃ | C₆H₅CH₂OCH₂ | H | $\overset{O}{\underset{\|}{C}}OCH_3$ | CONH₂ | Boc | C₆H₅CH₂ |
| 18 | N₃ | H | CH₃ | C₆H₅CH₂OCH₂ | H | $\overset{O}{\underset{\|}{C}}OCH_3$ | CONH₂ | Boc | C₆H₅CH₂ |
| 19 | NH₂ | H | CH₃ | HO—CH₂ | H | $\overset{O}{\underset{\|}{C}}OCH_3$ | CONH₂ | Boc | H |
| 20 | H, St—N | H | CH₃ | HO—CH₂ | H | $\overset{O}{\underset{\|}{C}}OCH_3$ | CONH₂ | Boc | H |
| 21 | H, St—N | H | CH₃ | HO—CH₂ | H | $\overset{O}{\underset{\|}{C}}OCH_3$ | CONH₂ | H | H |
| 22 | H, St—N | H | CH₃ | HO—CH₂ | H | $\overset{O}{\underset{\|}{C}}OCH_3$ | CONH₂ | QS-3 | H |
| 23 | C₆H₅CH(O—) | | CH₃ | C₆H₅CH₂OCH₂ | H | $\overset{O}{\underset{\|}{C}}OCH(CH_3)_2$ | CONH₂ | Boc | C₆H₅CH₂ |
| 24 | OH | H | CH₃ | C₆H₅CH₂OCH₂ | H | $\overset{O}{\underset{\|}{C}}OCH(CH_3)_2$ | CONH₂ | Boc | C₆H₅CH₂ |
| 25 | p-CH₃C₆H₅SO₃ | H | CH₃ | C₆H₅CH₂OCH₂ | H | $\overset{O}{\underset{\|}{C}}OCH(CH_3)_2$ | CONH₂ | Boc | C₆H₅CH₂ |
| 26 | N₃ | H | CH₃ | C₆H₅CH₂OCH₂ | H | $\overset{O}{\underset{\|}{C}}OCH(CH_3)_2$ | CONH₂ | Boc | C₆H₅CH₂ |
| 27 | NH₂ | H | CH₃ | HO—CH₂ | H | $\overset{O}{\underset{\|}{C}}OCH(CH_3)_2$ | CONH₂ | Boc | H |
| 28 | H, QS-10-N | H | CH₃ | HO—CH₂ | H | $\overset{O}{\underset{\|}{C}}OCH(CH_3)_2$ | CONH₂ | Boc | H |
| 29 | H, QS-10-N | H | CH₃ | HO—CH₂ | H | $\overset{O}{\underset{\|}{C}}OCH(CH_3)_2$ | CONH₂ | H | H | thoxy-5-methyl-1,4-benzoquinon-6-yl)decanoyl}amino-D-glucopyranos-3-O-yl]-D-propionyl-L-valyl-D-isoglutaminate (540 mg, 0.6 mmol), followed by the addition of 9 N hydrochloric acid-dioxane (1 ml). The reaction was carried out at room temperature for 20 minutes and petroleum ether was added to the solution. The resulting precipitate was filtered to give 515 mg of methyl 2-[2-amino-2,6-dideoxy-6-{10-(2,3-dimethoxy-5-methyl-1,4-benzoquinon-6-yl)decanoyl}amino-D-glucopyranos-3-O-yl]-D-propionyl-L-valyl-D-isoglutaminate hydrochloride. m.p. 97°–98° C. $[\alpha]_D^{22} +36.9°$ (c 0.5, ethanol). $Rf^1 = 0.20$, $Rf^2 = 0.62$.

Elemental analysis for $C_{39}H_{63}N_5O_{14} \cdot HCl \cdot \frac{1}{2}H_2O$: Calcd.: C, 53.75; H, 7.52; N, 8.04. Found: C, 53.72; H, 7.83; N, 7.99.

EXAMPLE 28

In N,N-dimethylformamide (0.5 ml) were dissolved methyl 2-[2-amino-2,6-dideoxy-6-{10-(2,3-dimethoxy-5-methyl-1,4-benzoquinon-6-yl)decanoyl}amino-D-glucopyranos-3-O-yl]-D-propionyl-L-valyl-D-isoglutaminate hydrochloride (83 mg, 0.1 mmol), p-nitrophenyl stearate (81 mg, 0.2 mmol) and N-ethylmorpholine (0.026 ml), and the reaction is carried out at room temperature for 24 hours. The solvent was evaporated and, as in Example 19, the residue was purified by silica gel TLC (Merck, 10 cm×20 cm) using a 25:3:2 (v/v) mixture of chloroform, acetone and methanol as the solvent system. The product was further purified by gel chromatography on Sephadex LH-20 (column size 1.5×90 cm: elution solvent, ethanol). The fractions containing the desired compound were pooled and the solvent was evaporated. The residue was lyophilized from t-butanol to give 68 mg of methyl 2-[2,6-dideoxy-6-{10-(2,3-dimethoxy-5-methyl-1,4-benzoquinon-6-yl)decanoyl}amino-2-stearoylamino-D-glucaopyranos-3-O-yl]-D-propionyl-L-valyl-D-isoglutaminate as yellow flakes. $[\alpha]_D^{22} +16.9°$ (c 0.5, ethanol). $Rf^1 = 0.64$, $Rf^3 = 0.17$, $Rf^4 = 0.73$.

Elemental analysis for $C_{57}H_{97}N_5O_{15}$: Calcd.: C, 62.67; H, 8.95; N, 6.41. Found: C, 62.56; H, 9.04; N, 6.43.

The compounds (X) set forth in Table 2 were prepared by the procedures described in Examples 29 to 72. The substituents on the respective compounds were designated by the following abbreviations.

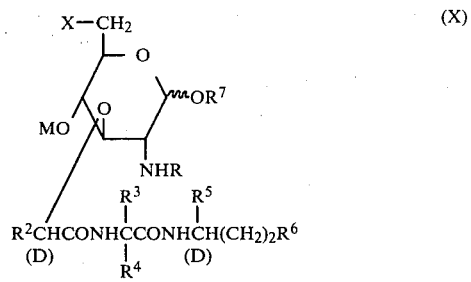

TABLE 2

| Compd. No. | X | M | $R^2$ | $R^3$ | $R^4$ | $R^6$ | $R^5$ | R | $R^7$ |
|---|---|---|---|---|---|---|---|---|---|
| 1 | H, QS-10-N | H | $CH_3$ | $CH_3$\CH/$CH_3$ | H | O‖COCH$_3$ | $CONH_2$ | QS-10 | H |
| 2 | H, St—N | H | $CH_3$ | $CH_3$\CH/$CH_3$ | H | O‖COCH$_3$ | $CONH_2$ | Boc | H |
| 3 | H, St—N | H | $CH_3$ | $CH_3$\CH/$CH_3$ | H | O‖COCH$_3$ | $CONH_2$ | H | H |
| 4 | H, St—N | H | $CH_3$ | $CH_3$\CH/$CH_3$ | H | O‖COCH$_3$ | $CONH_2$ | QS-10 | H |
| 5 | Benzyl 2-butyloxycarbonylamino-2-deoxy-4,6-benzylidene-α-D-glucopyranoside | | | | | | | | |
| 6 | 2-Benzyl 2-t-butyloxycarbonylamino-2-deoxy-4,6-O-benzylidene-α-D-glucopyranosid-3-O-yl)-D-propionic acid | | | | | | | | |
| 7 | $C_6H_5$\CH/O\ | | $CH_3$ | $CH_3$\CH/$CH_3$ | H | O‖COCH$_2$C$_6$H$_5$ | $CONH_2$ | Boc | $C_6H_5CH_2$ |
| 8 | OH | H | $CH_3$ | $CH_3$\CH/$CH_3$ | H | O‖COCH$_2$C$_6$H$_5$ | $CONH_2$ | Boc | $C_6H_5CH_2$ |
| 9 | p-$CH_3C_6H_5SO_3$ | H | $CH_3$ | $CH_3$\CH/$CH_3$ | H | O‖COCH$_2$C$_6$H$_5$ | $CONH_2$ | Boc | $C_6H_5CH_2$ |
| 10 | $N_3$ | H | $CH_3$ | $CH_3$\CH/$CH_3$ | H | O‖COCH$_2$C$_6$H$_5$ | $CONH_2$ | Boc | $C_6H_5CH_2$ |

TABLE 2-continued

| Compd. No. | X | M | R² | R³ | R⁴ | R⁶ | R⁵ | R | R⁷ |
|---|---|---|---|---|---|---|---|---|---|
| 30 | H, QS-10-N | H | CH₃ | HO—CH₂ | H | $\underset{\underset{CH_3}{\overset{CH_3}{\diagup}}}{\overset{O}{\underset{\|}{COCH}}}$ | CONH₂ | Far | H |
| 31 | Benzyl 2-benzyloxycarbonylamino-2-deoxy-4,6-O-isopropylidene-α-D-glucopyranoside | | | | | | | | |
| 32 | 2-(benzyl 2-benzyloxycarbonylamino-2-deoxy-4,6-O-isopropylidene-α-D-glycopyranosid-3-O-yl)-D-propionic acid | | | | | | | | |
| 33 | $\underset{O}{\overset{CH_3\diagdown\diagup CH_3}{C}}$ | CH₃ | CH₃ | CH₃ | CH₃ | $\underset{COCH_2C_6H_5}{\overset{O}{\|}}$ | CONH₂ | Z | C₆H₅CH₂ |
| 34 | OH | H | CH₃ | CH₃ | CH₃ | $\underset{COCH_2C_6H_5}{\overset{O}{\|}}$ | CONH₂ | Z | C₆H₅CH₂ |
| 35 | p-CH₃C₆H₅SO₃ | H | CH₃ | CH₃ | CH₃ | $\underset{COCH_2C_6H_5}{\overset{O}{\|}}$ | CONH₂ | Z | C₆H₅CH₂ |
| 36 | N₃ | H | CH₃ | CH₃ | CH₃ | $\underset{COCH_2C_6H_5}{\overset{O}{\|}}$ | CONH₂ | Z | C₆H₅CH₂ |
| 37 | NH₂ | H | CH₃ | CH₃ | CH₃ | $\underset{COH}{\overset{O}{\|}}$ | CONH₂ | H | H |
| 38 | H, KS-9-N | H | CH₃ | CH₃ | CH₃ | $\underset{COH}{\overset{O}{\|}}$ | CONH₂ | KS-9 | H |
| 39 | $\underset{O}{\overset{CH_3\diagdown\diagup CH_3}{C}}$ | CH₃ | CH₃ | C₆H₅CH₂OCH\|CH₃ | H | $\underset{COCH_3}{\overset{O}{\|}}$ | CONH₂ | Z | C₆H₅CH₂ |
| 40 | OH | H | CH₃ | C₆H₅CH₂OCH\|CH₃ | H | $\underset{COCH_3}{\overset{O}{\|}}$ | CONH₂ | Z | C₆H₅CH₂ |
| 41 | p-CH₃C₆H₅SO₃ | H | CH₃ | C₆H₅CH₂OCH\|CH₃ | H | $\underset{COCH_3}{\overset{O}{\|}}$ | CONH₂ | Z | C₆H₅CH₂ |
| 42 | N₃ | H | CH₃ | C₆H₅CH₂OCH\|CH₃ | H | $\underset{COCH_3}{\overset{O}{\|}}$ | CONH₂ | Z | C₆H₅CH₂ |
| 43 | NH₂ | H | CH₃ | HOCH\|CH₃ | H | $\underset{COCH_3}{\overset{O}{\|}}$ | CONH₂ | H | H |
| 44 | H, ES-10-N | H | CH₃ | HOCH\|CH₃ | H | $\underset{COCH_3}{\overset{O}{\|}}$ | CONH₂ | ES-10 | H |

TABLE 3

| Example No. | Starting Compound (Comp. No.) | Method (Example No.) | Object Compound (X) (Comp. No.) | Melting point | $[\alpha]_D$* | Rf value | Elemental analysis** | Reference |
|---|---|---|---|---|---|---|---|---|
| 29 | Ex. 28 | 28 | 1 | | +15.9° (A) | Rf¹ = 0.62<br>Rf³ = 0.16<br>Rf⁴ = 0.72 | C₅₈H₈₉N₅O₁₉<br>C60.03 H7.73 N6.06<br>60.00 7.89 6.03 | |
| 30 | Ex. 25 | 26 | 2 | 96–98° C. | +24.3° (A) | Rf¹ = 0.61<br>Rf³ = 0.17<br>Rf⁴ = 0.61 | C₄₃H₇₉N₅O₁₂ . ½ H₂O<br>C59.56 H9.30 N8.08<br>59.48 9.41 8.09 | |
| 31 | 2 | 27 | 3 | 133–135° C. | +48.9° (A) | Rf¹ = 0.12<br>Rf² = 0.74 | C₅₆.₈₀ H9.15 N8.72<br>56.75 9.02 8.78 | HCl salt |
| 32 | 3 | 28 | 4 | | +14.6° (A) | Rf¹ = 0.62<br>Rf³ = 0.17<br>Rf⁴ = 0.69 | C₅₇H₉₇N₅O₁₅<br>C62.67 H8.95 N6.41<br>62.77 9.21 6.47 | |
| 33 | *** | 19 | 5 | 169–170° C. | +106.2° (A) | Rf³ = 0.81<br>Rf⁴ = 0.90 | C₂₅H₃₁NO₇ . ½ H₂O<br>C64.36 H6.91 N3.00<br>63.98 6.82 2.95 | |
| 34 | 5 | 20 | 6 | 186–187° C. | +100.0° (A) | Rf¹ = 0.85<br>Rf⁴ = 0.45 | C₂₈H₃₅NO₉<br>C63.50 H6.66 N2.65<br>63.34 6.58 2.60 | |
| 35 | 6 | 21 | 7 | 220–221° C. | +88.2° (B) | Rf³ = 0.47<br>Rf⁴ = 0.93 | C₄₅H₅₈N₄O₁₂<br>C63.81 H6.90 N6.62<br>63.54 7.11 6.58 | |
| 36 | 7 | 22 | 8 | 152–153° C. | +89.9° (B) | Rf¹ = 0.54<br>Rf⁴ = 0.60 | C₃₈H₅₄N₄O₁₂<br>C60.01 H7.17 N7.38<br>60.03 7.11 7.51 | |
| | | | | | | Rf¹ = 0.80 | C₄₅H₆₀N₄O₁₄S | |

TABLE 3-continued

| Example No. | Starting Compound (Comp. No.) | Method (Example No.) | Object Compound (X) (Comp. No.) | Melting point | $[\alpha]_D$* | Rf value | Elemental analysis** | Reference |
|---|---|---|---|---|---|---|---|---|
| 37 | 8 | 23 | 9 | 118–120° C. | +70.8° (B) | $Rf^4 = 0.81$ | C59.19 H6.62 N6.14 S3.51<br>59.21 6.48 6.17<br>3.81 | |
| 38 | 9 | 24 | 10 | 115–116° C. | +75.2° (B) | $Rf^1 = 0.68$<br>$Rf^3 = 0.23$<br>$Rf^4 = 0.71$<br>$Rf^2 = 0.12$ | $C_{38}H_{53}N_7O_{11} \cdot \frac{1}{2} H_2O$<br>C57.56 H6.86 N12.36<br>57.73 6.92 12.37 | |
| 39 | 10 | 25 | 11 | | | | | |
| 40 | 11 | 26 | 12 | | +23.2° (A) | $Rf^1 = 0.27$<br>$Rf^2 = 0.73$ | $C_{43}H_{69}N_5O_{16} \cdot \frac{1}{2} H_2O$<br>C56.07 H7.66 N7.60<br>56.11 7.97 7.76 | Trifluoroacetate |
| 41 | 12 | 27 | 13 | | | $Rf^2 = 0.51$ | | |
| 42 | 13 | 28 | 14 | | +24.2° (A) | $Rf^1 = 0.46$<br>$Rf^4 = 0.07$ | $C_{57}H_{87}N_5O_{17}$<br>C61.43 H7.87 N6.29<br>61.44 8.21 6.33 | |
| 43 | ** | 21 | 15 | 218° C. | +79.2° (B) | $Rf^3 = 0.36$<br>$Rf^4 = 0.82$ | $C_{44}H_{56}N_4O_{13}$<br>C62.25 H6.65 N6.60<br>62.38 6.45 6.41 | |
| 44 | 15 | 22 | 16 | 183–183.5° C. | +82.2° (A) | $Rf^4 = 0.59$ | $C_{35}H_{54}N_4O_{13}$<br>C58.41 H6.89 N7.36<br>58.52 6.74 7.35 | |
| 45 | 16 | 23 | 17 | 68–69° C. | +68.9° (A) | $Rf^4 = 0.74$ | $C_{44}H_{58}N_4O_{15}S$<br>C57.76 H6.39 N6.12 S3.50<br>57.71 6.61 6.13<br>3.27 | |
| 46 | 17 | 24 | 18 | 165–167° C. | +80.8° (A) | $Rf^4 = 0.68$ | $C_{37}H_{51}N_7O_{12}$<br>C56.55 H6.54 N12.47<br>56.41 6.76 12.22 | |
| 47 | 18 | 25 | 19 | | | $Rf^5 = 0.51$ | | Acetate |
| 48 | 19 | 26 | 20 | | +17.8° (A) | $Rf^5 = 0.84$ | $C_{41}H_{75}N_5O_{13} \cdot H_2O$<br>C56.99 H8.98 N8.11<br>56.97 8.78 8.10 | |
| 49 | 20 | 27 | 21 | | | $Rf^5 = 0.58$ | | Trifluoroacetate |
| 50 | 21 | 28 | 22 | | +20.8° (A) | $Rf^4 = 0.31$<br>$Rf^5 = 0.81$ | $C_{48}H_{79}N_5O_{16} \cdot H_2O$<br>C57.64 H8.16 N7.00<br>57.24 7.83 7.13 | |
| 51 | ** | 21 | 23 | 204–206° C. | +73.7° (B) | $Rf^1 = 0.81$<br>$Rf^2 = 0.87$ | $C_{46}H_{59}N_4O_{13} \cdot \frac{1}{2} H_2O$<br>C62.43 H6.83 N6.33<br>62.47 7.04 6.42 | |
| 52 | 23 | 22 | 24 | 150–153° C. | +81.2° (B) | $Rf^1 = 0.63$<br>$Rf^2 = 0.59$ | $C_{39}H_{55}N_4O_{13} \cdot \frac{1}{2} H_2O$<br>C58.78 H7.08 N7.03<br>59.03 7.18 7.12 | |
| 53 | 24 | 23 | 25 | 78–80° C. | +66.6° (B) | $Rf^1 = 0.70$<br>$Rf^3 = 0.23$<br>$Rf^4 = 0.73$ | $C_{46}H_{61}N_4O_{15}S$<br>C58.64 H6.53 N5.95 S3.40<br>58.37 6.56 5.95<br>3.35 | |
| 54 | 25 | 24 | 26 | 129–130° C. | +69.7° (B) | $Rf^3 = 0.20$<br>$Rf^4 = 0.77$ | $C_{39}H_{54}N_7O_{12}$<br>C57.62 H6.70 N12.06<br>57.33 6.93 11.81 | |
| 55 | 26 | 25 | 27 | | | $Rf^2 = 0.26$ | | Acetate |
| 56 | 27 | 26 | 28 | | +15.7° (A) | $Rf^1 = 0.28$<br>$Rf^4 = 0.45$ | $C_{44}H_{71}N_5O_{17} \cdot \frac{1}{2} H_2O$<br>C55.56 H7.63 N7.36<br>55.41 7.63 7.19 | |
| 57 | 28 | 27 | 29 | | | $Rf^2 = 0.49$ | | Trifluoroacetate |
| 58 | 29 | 28 | 30 | | +15.3° (A) | $Rf^1 = 0.49$<br>$Rf^4 = 0.49$ | $C_{55}H_{87}N_5O_{16}$<br>C61.49 H8.16 N6.52<br>61.69 8.40 6.44 | |
| 59 | ** | 19 | 31 | sirup | +90.4° (A) | $Rf^4 = 0.88$ | $C_{24}H_{29}NO_7$<br>C65.00 H6.59 N3.16<br>64.79 6.28 3.12 | |
| 60 | 31 | 20 | 32 | sirup | +87.6° (A) | $Rf^3 = 0.31$ | $C_{27}H_{33}NO_9$<br>C62.90 H6.45 N2.72<br>62.96 6.44 2.45 | |
| 61 | 32 | 21 | 33 | 68° C. | +72.8° (A) | $Rf^3 = 0.41$ | $C_{43}H_{54}N_4O_{12} \cdot \frac{1}{2} H_2O$<br>C62.38 H6.70 N6.77<br>62.19 6.67 6.77 | |

TABLE 3-continued

| Example No. | Starting Compound (Comp. No.) | Method (Example No.) | Object Compound (X) (Comp. No.) | Melting point | $[\alpha]_D$* | Rf value | Elemental analysis** | Reference |
|---|---|---|---|---|---|---|---|---|
| 62 | 33 | 22 | 34 | 77° C. | +39.4° (A) | $Rf^4 = 0.40$ | $C_{40}H_{50}N_4O_{12}$<br>C61.69 H6.47 N7.19<br>61.71 6.49 7.48 | |
| 63 | 34 | 23 | 35 | 82–83° C. | +66.8° (A) | $Rf^4 = 0.74$ | $C_{47}H_{56}N_4O_{14}S$<br>C60.50 H6.05 N6.00<br>S3.44<br>60.32 6.12 6.17<br>3.29 | |
| 64 | 35 | 24 | 36 | 62–64° C. | +57.8° (A) | $Rf^4 = 0.65$ | $C_{40}H_{49}N_7O_{11} \cdot \frac{1}{2} H_2O$<br>C59.10 H6.20 N12.06<br>59.06 6.11 12.22 | |
| 65 | 36 | 25 | 37 | | | $Rf^5 = 0.23$ | | Trifluoroacetate |
| 66 | 37 | 26 | 38 | | +14.4° (A) | $Rf^2 = 0.39$<br>$Rf^4 = 0.11$ | $C_{58}H_{77}N_5O_{15} \cdot H_2O$<br>C63.20 H7.22 N6.35<br>63.27 7.14 6.10 | |
| 67 | *** | 21 | 39 | 78° C. | +76.6° (A) | $Rf^3 = 0.39$ | $C_{44}H_{56}N_4O_{13} \cdot H_2O$<br>C60.95 H6.82 N6.46<br>60.72 6.50 6.79 | |
| 68 | 39 | 22 | 40 | 145.5–147° C. | +41.2° (A) | $Rf^4 = 0.49$ | $C_{41}H_{52}N_4O_{13} \cdot H_2O$<br>C59.55 H6.58 N6.78<br>59.53 6.32 7.05 | |
| 69 | 40 | 23 | 41 | 84–86° C. | +65.8° (A) | $Rf^4 = 0.72$ | $C_{48}H_{58}N_4O_{15}S$<br>C59.86 H6.07 N5.82<br>S3.33<br>59.65 6.31 6.29<br>3.38 | |
| 70 | 41 | 24 | 42 | 77° C. | +69.6° (A) | $Rf^4 = 0.63$ | $C_{41}H_{51}N_7O_{12} \cdot \frac{1}{2} H_2O$<br>C58.42 H6.21 N11.63<br>58.20 6.09 11.90 | |
| 71 | 42 | 25 | 43 | | | $Rf^5 = 0.27$ | | Acetate |
| 72 | 43 | 26 | 44 | | +15.0° (A) | $Rf^4 = 0.32$<br>$Rf^5 = 0.77$ | $C_{57}H_{87}N_5O_{16} \cdot \frac{1}{2} H_2O$<br>C61.83 H8.01 N6.32<br>61.57 7.90 6.58 | |

* (A) (c 0.5, ethanol)
(B) (c 0.5, N,N-dimethylformamide) Determined at a temperature 19° C.–27° C.
** Calculated values in each top rows, found values in each bottom rows.
*** Benzyl 2-amino-2-deoxy-4,6-O-benzylidene-α-D-glucopyranoside
**
** The starting compound used is the same to the starting compound in the cited example.

EXAMPLE 73

Two mg of methyl 2-{2-acetamido-2,6-dideoxy-6-[10-(2,3-dimethoxy-5-methyl-1,4-benzoquinon-6-yl)decanoyl]amino-D-glucopyranos-3-O-yl}-D-propionyl-L-valyl-D-isoglutaminate which had been treated with 10 μg of squalene was vigorously homogenized with 1 ml of a phosphate buffered physiological saline solution containing 0.2% Tween 80 or 1 ml of physiological saline solution containing 0.2% Tween 80 to prepare an oil-in-water emulsion which is used as an injectable preparation in a dose of 0.5 ml per subject.

EXAMPLE 74

Eight mg of 2-(2-acetamido-2,6-didexoy-6-mycoloylamino-D-glucopyranos-3-O-yl)-D-propionyl-L-valyl-D-isoglutamine was suspended in 3.5 ml of a phosphate buffered physiological saline solution and the solution was sterilized. The solution was added dropwise to 0.5 ml of a mixture of hydrogenated vegetable triglyceride (Miglyol 812 and mannitol monooleate (17:3) while vigorously stirring to prepare an oil-in-water emulsion which is used as an injectable preparation in a dose of 0.5 ml per subject.

EXAMPLE 75

Five hundred mg of methyl 2-(2-acetamido-2,6-dideoxy-6-amino-D-glucopyranos-3-O-yl)-D-propionyl-L-valyl-D-isoglutaminate hydrochloride and 5 g of mannitol were dissolved in distilled water and the total volume was made to 1000 ml. After being sterilized by filtration, the solution was distributed into vials in an amount of 2 ml per vial, followed by freeze-drying. The resulting preparation is dissolved in a physiological saline solution prior to use for injection.

What is claimed is:

1. A compound of the formula:

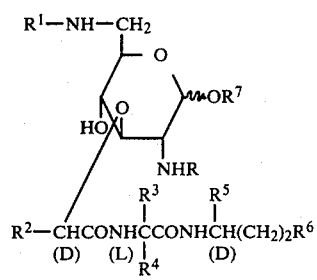

wherein
R is hydrogen or an organic acid residue having an acyclic group of up to $C_{80}$ or lower alkoxycarbonyl;
$R^1$ is hydrogen or acyl having an acyclic group of up to $C_{80}$;
$R^2$ is hydrogen or $C_{1-6}$ alkyl;

$R^3$ and $R^4$ are each hydrogen or $C_{1-6}$ alkyl which may be substituted with hydroxyl;
$R^5$ is $CONH_2$, $COOH$ or $COO\text{-}(C_{1-3}\text{alkyl})$;
$R^6$ is $COOH$ or $COO\text{-}(C_{1-3}\text{alkyl})$;
$R^7$ is hydrogen or $C_{1-2}$ alkyl substituted with phenyl; and
(D) and (L) each indicate configurations if their respective carbon atoms are asymmetric
or a salt thereof.

2. A compound according to claim 1, wherein R is acyl having an acyclic hydrocarbon group, the terminal of which is substituted with 6-membered cyclic hydrocarbon group.

3. A compound according to claim 1, wherein R is $C_{2-3}$ acyl.

4. A compound according to claim 1, wherein $R^1$ is acyl having an acyclic hydrocarbon group, the terminal of which is substituted with 6-membered cyclic hydrocarbon group.

5. A compound according to claim 1, wherein $R^1$ is $\omega$-(2,3-dimethoxy-5-methyl-1,4-benzoquinon-6-yl)-$C_{3-10}$ alkanoyl.

6. A compound according to claim 1, wherein $R^1$ is mycoloyl.

7. A compound according to claim 1, wherein $R^5$ is carbamoyl and $R^6$ is hydroxylcarbonyl.

8. A compound according to claim 1, said compound being 2-(2-acetamido-2,6-dideoxy-6-mycoloylamino-D-glucopyranos-3-O-yl)-D-propionyl-L-alkanyl-D-isoglutamine.

9. A compound according to claim 1, said compound being methyl 2-[2-acetamido-2,6-dideoxy-6-{10-(2,3-dimethoxy-5-methyl-1,4-benzoquinon-6-yl)decanoyl}-amino-D-glucopyranos-3-O-yl]-D-propionyl-L-valyl-D-isoglutaminate.

10. A compound according to claim 1, said compound being methyl 2-[2,6-dideoxy-6-{10-(2,3-dimethoxy-5-methyl-1,4-benzoquinon-6-yl)decanoyl}amino-2-stearoylamino-D-glucopyranos-3-O-yl]-D-propionyl-L-valyl-D-isoglutaminate.

11. A compound according to claim 1, said compound being 2-[2,6-dideoxy-2,6-di{10-(2,3-dimethoxy-5-methyl-1,4-benzoquinon-6-yl)decanoyl}amino-D-glucopyranos-3-O-yl]-D-propionyl-L-valyl-D-isoglutamine.

12. A compound according to claim 1, wherein $R^5$ is $CONH_2$ or $COO\text{-}(C_{1-3}\text{alkyl})$.

13. A method for stimulating the immunological function of a warm-blooded aminal which comprises administering to said animal an effective amount of a compound of the formula:

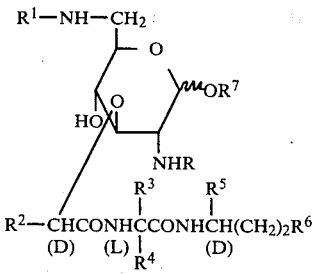

wherein
R is hydrogen, an organic acid residue having an acyclic group of up to $C_{80}$ or lower alkoxycarbonyl;
$R^1$ is hydrogen or acyl having an acyclic group of up to $C_{80}$;
$R^2$ is hydrogen or $C_{1-6}$alkyl;
$R^3$ and $R^4$ are each hydrogen or $C_{1-6}$ alkyl which may be substituted with hydroxyl;
$R^5$ is $CONH_2$, $COOH$ or $COO\text{-}(C_{1-3}\text{alkyl})$;
$R^6$ is $COOH$ or $COO\text{-}(C_{1-3}\text{alkyl})$;
$R^7$ is hydrogen or $C_{1-2}$alkyl substituted with phenyl; and
(D) and (L) each indicate configurations if their respective carbon atoms are asymmetric
or a salt thereof.

* * * * *